(12) United States Patent
Baird et al.

(10) Patent No.: US 9,206,213 B2
(45) Date of Patent: Dec. 8, 2015

(54) METHODS FOR PATHOGEN DETECTION AND DISEASE TREATMENT

(71) Applicant: Bangor University, Bangor (GB)

(72) Inventors: Mark Stephen Baird, Bangor (GB); Juma'a Raheem Najeem Al Dulayymi, Bangor (GB); Johan Adriaan Marc Grooten, Ghent (BE); Seppe Vander Beken, Ghent (BE); Maximilliano Maza-Inglesias, Bangor (GB)

(73) Assignee: Bangor University, Bangor (GB)

( * ) Notice: Subject to any disclaimer, the term of this patent is extended or adjusted under 35 U.S.C. 154(b) by 29 days.

(21) Appl. No.: 14/100,423

(22) Filed: Dec. 9, 2013

(65) Prior Publication Data

US 2014/0178434 A1 Jun. 26, 2014

Related U.S. Application Data

(62) Division of application No. 13/146,997, filed as application No. PCT/GB2010/050146 on Jan. 29, 2010, now abandoned.

(51) Int. Cl.
*A61K 31/7024* (2006.01)
*A61K 39/04* (2006.01)
*C07H 13/04* (2006.01)
*G01N 33/569* (2006.01)
*C07H 23/00* (2006.01)

(52) U.S. Cl.
CPC ............ *C07H 13/04* (2013.01); *A61K 31/7024* (2013.01); *A61K 39/04* (2013.01); *C07H 23/00* (2013.01); *G01N 33/5695* (2013.01)

(58) Field of Classification Search
None
See application file for complete search history.

(56) References Cited

U.S. PATENT DOCUMENTS 5,721,109 A 2/1998 Yano et al.

FOREIGN PATENT DOCUMENTS

| EP | 0261248 A1 | 3/1988 |
|---|---|---|
| JP | 2002179574 A | 6/2002 |
| JP | 2002179577 A | 6/2002 |
| WO | 2009130506 A2 | 10/2009 |
| WO | 2009130508 A1 | 10/2009 |

OTHER PUBLICATIONS

Al Dulayymi et al., "The synthesis of single enantiomers of a major a-mycolic acid acid of *Mycobacterium tuberculosis*," 2003, pp. 228-229, Chemical Communication.
Al Dulayymi et al., "The first synthesis of single enantiomers of the major methoxymycolic acid of *Mycobacterium tuberculosis*," 2007, pp. 2571-2592, ScienceDirect, Tetrahedron 63.
Al Dulayymi et al., "The synthesis of one enantiomer of the a-methyl-trans-cyclopropane unit of mycolic acids," 2006, pp. 4851-4862, ScienceDirect, Tetrahedron 62.
Al Dulayymi et al., "The synthesis of single enantiomers of meromycolic acids from mycobaterial wax esters," 2006, pp. 11867-11880, ScienceDirect, Tetrahedron 62.
Bekierkunst et al., "Immunotherapy of Cance with Nonliving BCG and Fractions Derived from Mycobacteria: Role of Cord Factor (Trehalose-6,6' -Dimycolate) in Tumor Regression," 1974, pp. 1044-1050, Infection and Immunity, American Society for Microbiology, vol. 10, No. 5.
Fujita et al., "Direct molecular mass determination of trehalose monomycolate from 11 species of mycobacteria by MALDI-TOF mass spectrometry," 2005, pp. 1443-1452, Microbiology 151.
Fujita et al., "Intact molecular characterization of cord factor (trehalose 6,6'-dimycolate) from nine species of mycobacteria by MALDI-TOF mass spectrometry," 2005, pp. 3403-3416, Microbiology 151.
Kai et al., "Identification of trehalose dimycolate (cord factor) in *Mycobacterium leprae*," 2007, pp. 3345-3350, FEBS Letters 581.
Koza et al., "The first synthesis of single anantiomers of ketomycolic acids," 2007, pp. 2165-2169, ScienceDirect, Tetrahedron Letters 48.
Matsunago et al., "Mycolyl glycolipids stimulate macrophages to release a chemotactic factor," 1990, pp. 49-53, FEMS Microbiology Letters 67.
Nishizawa et al., "Efficient Syntheses of a Series of Trehalose Dimycolate (TDM)/Trehalose Dicorynomycolate (TDCM) Analogues and DMTheir Interleukin-6 Level Enhancement Activity in Mice Sera," 2009, pp. 1627-1633, The Journal of Organic Chemistry.
Rao et al., "*Mycobacterium tuberculosis* controls host innate immune activation through cyclopropane modification of a glycolipid effector molecule," 2005, pp. 535-543, The Journal of Experimental Medicine.
Rao et al., "Trans-cyclopropanation of mycolic acids on trehalose dimycolate suppresses *Mycobacterium tuberculosis*-induced inflammation and virulence," 2006, pp. 1660-1667, The Journal of Clinical Investigation, vol. 116, No. 6.
Ryll et al., "Immunological Properties of Trehalose Dimycolate (Cord Factor) and Other Mycolic Acid-Containing Glycolipids—A Review," 2001, pp. 801-811, Microbiology Immunology vol. 45, No. 12.
Sakaguchi et al., "Trehalose 6,6'-Dimycolate (Cord Factor) Enhances Neovascularization through Vascular Endothelial Growth Factor Production by Neutrophils and Macrophages," 2000, pp. 2043-2052, Infection and Immunity, vol. 68, No. 4.
Toschi et al., "An improved procedure for the preparation of the β-hydroxy-a-alkyl fatty acid fragment of mycolic acids," 2006, pp. 3221-3227, ScienceDirect, Tetrahedron 62.
Watanabe et al., "Location of functional groups in mycobacterial meromycolate chains; the recognition of new structural principles in mycolic acids," 2002, pp. 1881-1902, Microbiology 148.
Watanabe et al., "Separation and characterization of individual mycolic acids in representative mycobacteria," 2001, pp. 1825-1837, Microbiology 147.

(Continued)

*Primary Examiner* — Layla Bland
(74) *Attorney, Agent, or Firm* — Hoffman Warnick LLC

(57) ABSTRACT

A method of preparing a compound of formula (III):

$$(M)_x\text{-}(S)_y\text{-}(M')_z \qquad (III)$$

wherein x is from 1 to 6, y is from 1 to 12, z is from 0 to 10, each M and each M' is independently a mycolic acid residue including a β-hydroxy acid moiety and each S is a monosaccharide unit; the method comprising reacting one or more mycolic acids with one or more saccharide units wherein the hydroxyl group of each β-hydroxy acid moiety is protected prior to reaction with the one or more saccharide units.

9 Claims, No Drawings

(56) References Cited

OTHER PUBLICATIONS

Yano et al., "Control of hair growth and follicle size by VEGF-mediated angiogenesis," 2001, pp. 409-417, The Journal of Clinical Investigation, vol. 107, No. 4.
Patent Cooperation Treaty, International Search Report for PCT/GB2010/050146 dated Jun. 9, 2011, 5 pages.
Al Dulayymi . et al., "The first unique synthetic mycobacterial cord factors", Jul. 2009, pp. 3702-3705, Tetrahedron Letters, vol. 50, No. 26 (XP26120596).
Kato et al., "Chemical Structure and Biochemical Activity of Cord Factor Analogs", 1971, pp. 364-370, European Journal of Biochemistry, vol. 22, No. 3 (XP-002640597).
Brochere-Ferreol et al., "Substances with cord factory activity. Sythesis of 6,6'—diesters of trehalose", Jan. 1958, pp. 714-717, Bulletin de la Societe Chimique de France, Societe Francaise de Chimie, Paris, France (XP-009149072).
Polonsky et al., "Cord Factor, a toxic lipide from *Mycobacterium tuberculosis*. Synthesis of cord factor-active substances (esters of trehalose and synthetic branched chain acids)", Jan. 1956, pp. 1471-1478, Bulletin de la Societe Chimique de Paris, Societe Franzaise de Chimie, Paris, France (XP-009149068).
Parant et al., "Nonspecific Immunostimulant Activities of Synthetic Trehalose-6,6'-Diesters (Lower Homologs of Cord Factor)", Apr. 1978, pp. 12-19, Infection and Immunity, American Society for Microbiology, Washington, US. vol. 20. No. 1 (XP-002539259).
Nishizawa et al., "Efficient Synthesis of a Series of Trehalose Dimycolate (TDM)/Trehalose Dicorynomycolate (TDCM) Analogues and Their Interleukin-6 Level Enhancement Activity in Mice Sera", Feb. 2007, pp. 1527-1633, Journal of Organic Chemistry, American Chemical Society, vol. 72. No. 5 (XP-009111529).
Patent Cooperation Treaty, International Preliminary Report on Patentability and Written Opinion of the International Searching Authority for PCT/GB2010/050146 dated Aug. 2, 2011, 9 pages.
Bland, Office Action Communication for U.S. Appl. No. 13/146,997 dated Aug. 9, 2013, 10 pages.
Bland, Office Action Communication for U.S. Appl. No. 13/146,997 dated Mar. 28, 2013, 17 pages.
Durand et al., "Phase Behaviour of Cord Factor and Related Bacterial Glycolipid Toxins," 1979, pp. 108-112, Eur. J. Biochem, 93.
Dulayymi et al., "The synthesis of a single enantiomer of a major a-mycolic acid of *M. tuberculosis*," 2005, pp. 11939-11951, Tetrahedron 61.

METHODS FOR PATHOGEN DETECTION AND DISEASE TREATMENT

CROSS-REFERENCE TO RELATED APPLICATIONS

This application is a divisional of co-pending U.S. patent application Ser. No. 13/146,997 filed on Jul. 29, 2011, which is a 371 National Stage Application of PCT/GB2010/050146 filed Jan. 29, 2010, which claims priority to GB Application No. 0901465.5 filed Jan. 29, 2009. The applications identified above are incorporated herein by reference in their entireties for all that they contain in order to provide continuity of disclosure.

The present invention relates to sugar esters of individual mycolic acids, to compositions comprising the same and to methods and uses relating thereto.

Mycolic acids are long chain fatty acid compounds typically having 60 to 90 carbon atoms and are found as components of the cells of mycobacteria. An example of such bacteria is *Mycobacterium tuberculosis*.

Two moieties can be distinguished in each mycolic acid: the main branch, or meromycolate moiety, and the mycolic motif, an α-alkyl β-hydroxy acid. The structure of the mycolic motif is common to each naturally occurring mycolic acid, except for minor variations in the length of the chain in the α-position. The two stereocentres in the α and β positions relative to the carboxylic group present in all natural mycolic acids have, when examined, always been found to both be in the (R)-configuration in these natural products. On the other hand, the meromycolate section, which generally contains two functionalities and three long chains (a, b, c in figure I), can be differently substituted in both the proximal (the one nearer the hydroxy-acid) and the distal position (further from the carboxylic acid).

FIG. I

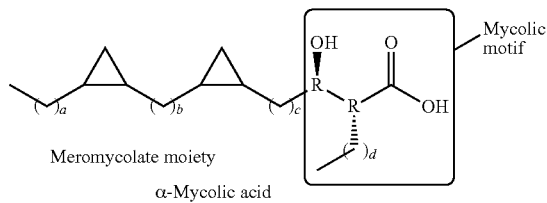

α-Mycolic acid

The mycolic acids are broadly separated into classes, according to the groups present in the meromycolate moiety. The proximal or distal functional groups can include cyclopropanes, double bonds, an epoxy group, a methoxy group, carbonyl group, carboxyl group or methyl group.

Examples of classes of mycolic acids (which in this specification may be referred to as MA) are shown in figure II and include α-MA (1), methoxy-MA (2), and keto-MA (3) all containing a cis-cyclopropane proximal to the hydroxy-acid; and corresponding structures (4) containing a proximal α-methyl-trans-cyclopropane.

FIG. II

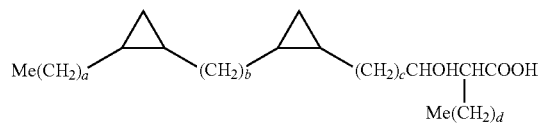

(1)

-continued (2)

(3)

(4)

X,Y = CH$_2$ or X = Me, Y = OMe
a = 15, 17, 18, 19
b = 10, 14, 16
c = 11, 15, 17, 19, 21
d = 21, 23

Details of many different compounds that are found in natural sources of mycolic acid are for example, given by M Watanabe, Y Aoyagi, H Mitome, T Fujita, H Naoki, M Ridell and D E Minnikin, *Microbiology* (2002), 148, 1881-1902; and M Watanabe, Y Aoyagi, M Ridell and D E Minnikin; *Microbiology* (2001), 147, 1825-1837.

Natural sources of mycolic acids, for example the cell walls of mycobacteria such as *Mycobacterium tuberculosis* include mixtures of different classes of compounds and different homologues, often as derivatives in which they are bonded to the wall of the cell.

In addition to the mycolic acids themselves, the cells of mycobacteria also contain compounds derived from the acid, for example sugar esters of mycolic acids. Naturally occurring sugar esters include trehalose-6,6'-dimycolate (which may be referred to as TDM and which are also known as "cord factors") and trehalose monomycolates (which may be referred to as TMM). However such sugar esters occur in nature as complex mixtures of different classes of mycolic acids and of different homologues within each class. Separation of individual compounds is very difficult and thus very little is known about the properties of the individual separated components. For example, most biological testing carried out previously has been done on mixtures extracted from natural sources of compounds or on "semi-synthetic" cord-factors prepared by attaching sometimes separated classes of mycolic acids to the sugar. The latter compounds still however contain mixtures of different homologues. Nevertheless tests on the mixtures have revealed interesting biological activity.

The biological activity of sugar esters of mycolic acids is vast and varied and has been extensively discussed in the prior art. In RyII R, Kumazawa Y, Yano I, *Microbiol. Immunol.* 45, 801-811, a number of immunomodifying effects of MA-containing glycolipids, in particular TDM, are discussed. For example, they are able to stimulate innate, early adaptive and both humoral and cellular adaptive immunity. The authors of this review consider that most functions can be associated with their ability to induce a wide range of chemokines (MCP-1, MIP-1α, IL-8) and cytokines (e.g., IL-12, IFN-γ, TNF-α, IL-4, IL-6, IL-10).

Sugar esters of mycolic acids have been found to show positive effects against a range of cancers—see for example Bekierkunst A, Wang L, Toubiana R, Lederer E Infect. Immun., 1974, 10, 1044; and Yano K, Brown L F, Detmar M, J. Clin. Invest., 2001, 107, 409. Due to the observed effects on the immune system, it is believed that these compounds may be useful in the treatment of autoimmune diseases.

U.S. Pat. No. 5,721,109 for example describes a method of diagnosing an infection caused by an acid-fast bacterium which comprises conducting an immunoassay on a sample of body fluid with a reagent which comprises a mycolic acid compound. The mycolic acids used are mixtures from natural sources or simple synthetic analogues.

Despite this considerable biological activity, samples of sugar esters of mycobacterial mycolic acids as single compounds have not previously been available and thus it has not been possible to establish with certainty which chemical species is responsible for a particular biological effect.

The identification of cord factors in mixtures extracted from natural products is a very tedious and time-consuming undertaking. For example analysis by mass spectroscopy is described in: "Identification of trehalose dimycolate (cord factor) in *Mycobacterium leprae*"; Masanori Kai, Yukiko Fujita, Yumi Maeda, Noboru Nakata, Shinzo Izumi, Ikuya Yano, Masahiko Makino; FEBS Letters 581 (2007) 3345-3350; "Direct molecular mass determination of trehalose monomycolate from 11 species of mycobacteria by MALDI-TOF mass spectrometry"; Yukiko Fujita, Takashi Naka, Takeshi Doi and Ikuya Yano; Microbiology (2005), 151, 1443-1452; and "Intact molecular characterization of cord factor (trehalose 6,6'-dimycolate) from nine species of mycobacteria by MALDI-TOF mass spectrometry"; Yukiko Fujita, Takashi Naka, Michael R. McNeil and Ikuya Yano; Microbiology (2005), 151, 3403-3416.

Given how difficult it can be to establish the identity of cord factors present in natural products and to separate individual molecular species it would be highly beneficial to be able to prepare compounds as single isomers where the identity of the compound being prepared is known.

Several methods have been reported by which 'semi-synthetic' cord factors may be reconstituted from natural mixtures of mycolic acids derived from bacteria, by re-forming the sugar esters in a number of ways. However, in each case a mixture has been obtained. The synthesis of model cord-factors including a less complex acid group has also been reported by Nishizowa et al *J. Org. Chem.*, 2007, 72(5), 1627-33). It is known that the structure of the mycolic acid unit affects the biological activity of the cord factor. Thus the preparation of single compounds matching those which are found in nature is highly desirable.

The present inventors have prepared synthetic compounds as single stereoisomers of a number of sugar esters of mycolic acids which are identical or closely analogous to single compounds found in the natural mixtures.

According to a first aspect of the present invention there is provided a method of preparing a compound of formula (III):

$$(M)_x\text{-}(S)_y\text{-}(M')_z \quad (III)$$

wherein x is from 1 to 6, y is from 1 to 12, z is from 0 to 10, each M and each M' is independently a mycolic acid residue including a β-hydroxy acid moiety and each S is a monosaccharide unit; the method comprising reacting one or more mycolic acids with one or more saccharide units wherein the hydroxyl group of each β-hydroxy acid moiety is protected prior to reaction with the one or more saccharide units.

In the method of the present invention one or more saccharide units is reacted with one or more mycolic acid units.

Preferably when the compound of formula (III) comprises more than one saccharide unit these are suitably first linked together prior to reaction with the mycolic acid compound(s). Many naturally occurring monosaccharides are commercially available as are common disaccharides and oligosaccharides. Thus the method of the present invention preferably comprises reacting a saccharide species with one or more mycolic acids. The saccharide species may comprise one or more saccharide units. Such saccharide species may be obtained from commercial sources or they may be prepared by reaction of one or more monosaccharide or disaccharide units.

In embodiments in which more than one mycolic acid unit is reacted these are preferably not reacted as a mixture.

Preferably the saccharide species is reacted with a first mycolic acid and then subsequently reacted with a second mycolic acid. It may optionally be subsequently reacted with a third, fourth, fifth or sixth mycolic acid etc but reactions with different mycolic acids are preferably sequential.

Suitable methods for preparing the mycolic acids starting materials are described in previous publications of the inventors. See for example Al Dulayymi J R, Baird M S and Roberts E, Chem Commun (Camb) 2003:228-9; Al Dulayymi J R, Baird M S and Roberts E., Tetrahedron 2005; 61:11939-11951; Al Dulayymi J R, Baird M S, Roberts E, Deysel M and Verschoor J., Tetrahedron 2007; 63:2571-2592; Al Dulayymi J R, Baird M S, Roberts E and Minnikin D E., Tetrahedron 2006; 62:11867-11880; Al-Dulayymi J R, Baird M S, Mohammed H, Roberts E and Clegg W., Tetrahedron 2006; 62:4851-4862; Koza G, Baird M S., Tetrahedron Letters 2007; 48:2165-2169; and Toschi G, Baird M S., Tetrahedron 2006; 62:3221-3227.

Alternatively the individual mycolic acid starting materials may be obtained by separation of mixtures extracted from natural sources.

The mycolic acid starting materials include a β-hydroxy acid moiety in which the hydroxyl group is protected prior to reaction with the saccharide species. Any suitable protecting group maybe used and the selection of an appropriate protecting group for the reaction conditions is commonplace for the person skilled in the art. Preferably the hydroxyl group of the mycolic acid starting material is protected using a silyl protecting group. An especially preferred protecting group is tert-butyl-dimethysilyl. Protection of the hydroxyl group may be achieved by a standard procedure known to those skilled in the art.

The hydroxyl protected acid is preferably reacted with a suitable saccharide species. Suitable saccharide species include monosaccharides, disaccharides and oligosaccharides. Monosaccharides and especially disaccharides are preferred.

Suitably all of the hydroxyl groups of the saccharide species are protected other than the one or more groups which are to be reacted with the mycolic acid compound.

Preferably one or more primary hydroxyl groups are not protected and all of remaining secondary hydroxyl groups are protected. Suitably each protected hydroxyl group of the saccharide species is protected with the same protecting group.

Preferred are silyl protecting groups, especially trimethylsilyl. Again the preparation of selectively protected saccharides is known to those skilled in the art and some compounds of this type are commercially available.

Preferably the method of the present invention comprises reacting a protected mycolic acid compound with a protected saccharide species.

The method of the present invention preferably involves an esterification reaction. The reaction of an acid and an alcohol to form an ester is a very well known reaction and any suitable method may be used. In a preferred method a coupling agent is used. Such coupling agents are well known to those skilled in the art and are typically used in the presence of a catalytic amount of 4-dimethylaminopyridine (or 4-DMAP). A preferred coupling agent is 1-(3-dimethyaminopropyl)-3-ethyl-carbodiimide hydrochloride (EDCl).

Suitably following the esterification reaction of the protected acid and protected saccharide the resultant product is deprotected. Removal of protecting groups is commonplace to the person skilled in the art. In the case of a silyl protecting group, a source of fluoride ion is typically used, for example tetrabutyl ammonium fluoride.

The method of the present invention may suitably comprise the steps of:
 (i) protecting the hydroxyl group of the -hydroxy acid moiety of a mycolic acid;
 (ii) reacting the protected acid produced in step (i) with a saccharide species;
 (iii) optionally reacting the product obtained in step (ii) with a further mycolic acid group in which the -hydroxy acid moiety is protected; and
 (iv) deprotecting the -hydroxy acid moiety of the mycolic acid(s).

In embodiments which include step (iii) the further mycolic acid may be the same as or different to the mycolic acid protected in step (i).

Optionally the method may include a step of preparing the saccharide species used in step (ii), for example from one or more monosaccharide and/or disaccharide units. Preferably all of the non-reacting hydroxyl groups of the saccharide species reacted in step (ii) are protected, for example as silyl ethers. The method may thus suitably include a step of deprotecting the remaining alcohol groups of the saccharide unit. This may be carried out before step (iv), after step (iv) or simultaneously with step (iv). For example a single deprotection step which removes all of the protecting groups could be carried out.

The method may comprise a step of purifying the product obtained in step (iv), However this is preferably a simple purification method carried out routinely. A specific advantage of the method of the present invention is that it may be used to prepare compounds of formula (III) in high purity.

In the method of the present invention the mycolic acid and saccharide starting materials used are suitably of high purity. In particular it is desired that each of the mycolic acid and saccharide starting materials comprises essentially a single isomer.

The method of the present invention may be used to prepare compounds which resemble those believed to be present in natural mixtures or it may be used to prepare compounds which have not previously been identified.

According to a second aspect of the presentation there is provided a compound prepared by the method of the first aspect. This compound is suitably provided in highly purified form.

The compounds of the second aspect of the present invention are suitably available in highly purified forms, preferably as single homologues and preferably as single regioisomers and as single stereoisomers. Suitably they are at least 90% pure, preferably at least 95% pure, for example at least 98% or 99% pure.

According to a third aspect of the present invention there is provided a composition comprising a compound of formula (III):

$$(M)_x\text{-}(S)_y\text{-}(M')_z \qquad (III)$$

wherein x is from 1 to 6, y is from 1 to 12, z is from 0 to 10, each M and each M' is independently a mycolic acid residue including a β-hydroxy acid moiety and each S is a monosaccharide unit.

Preferably the composition comprises at least 90 wt % of a compound of formula (III), preferably at least 95 wt %, more preferably at least 99 wt %. These amounts refer to the amount of a single compound present, preferably as a single isomer. Suitably substantially no homologues, regioisomers or stereoisomers are present.

The present invention further provides single compounds of formula (III) having a purity of at least 90%, preferably at least 95%, more preferably at least 99%.

Preferably x is from 1 to 4, preferably from 1 to 3, more preferably x is 1 or 2 and most preferably x is 1.

When x is greater than 1 and y is greater than 1, each M may be bonded to the same or different monosaccharide unit.

Preferably z is 0 to 6, preferably 0 to 4, more preferably 0 to 2, for example 0 or 1. Most preferably z is 1.

When z is greater than 1 and y is greater than 1, each M' may be bonded to the same or different monosaccharide unit.

Each M or M' is a mycolic acid residue. By this we mean to refer to the portion of the acid molecule other than the acidic proton.

Each M and M' may be the same or different. When x is greater than 1, each M may be the same or different. When z is greater than 1, each M' may be the same or different.

The compounds of formula (III) are sugar esters of mycolic acid. Thus each acidic unit of the mycolic acid residues M and/or M' is bonded to an alcoholic group of a monosaccharide unit to form an ester linkage. Preferably each M and/or M' is bonded to a primary alcoholic group of a monosaccharide unit.

Preferably y is between 1 and 6, preferably between 1 and 4, more preferably between 1 and 3. Most preferably y is 1 or 2, especially 2.

In some preferred embodiments the compound of formula (III) is an ester formed from one mycolic acid unit and one monosaccharide unit.

In some preferred embodiments, the compound of formula (III) is an ester formed from one mycolic acid unit and two monosaccharide units wherein the two monosaccharide units are joined to form a disaccharide. Thus in such embodiments the compound of formula (III) is an ester formed from one mycolic acid unit and a disaccharide.

In some preferred embodiments, the compound of formula (III) is an ester formed from two mycolic acid units and two monosaccharides, that is two mycolic acid units and a disaccharide. In such cases, the compound has the formula M-S—S-M' in which each monosaccharide unit S may be the same or different.

In some preferred embodiments the ratio of mycolic acid units (M and M' combined total) to monosaccharide units(s) is approximately 1:1.

In preferred embodiments x+z=y.

Preferably the or each monosaccharide unit S has from 3 to 8 carbon atoms, preferably 5 to 7 carbon atoms. Most preferably the or each monosaccharide unit has 6 carbon atoms. In preferred embodiments the or each monosaccharide unit S is an aldose.

Preferably each S is independently selected from allose, altrose, galactose, glucose, gulose, idose, mannose, talose, fructose, psicose, sorbose, and tagatose. Most preferably each S is independently selected from allose, altrose, galactose, glucose, gulose, idose, mannose and talose. In especially preferred embodiments each S is independently selected from glucose and mannose. Most preferably each S is glucose.

Each monosaccharide unit may be present as the D or L isomer. Preferably each is present as the natural D isomer. Each monosaccharide unit may be present as the α form or the β form.

In preferred embodiments, y is 2 and the compound of formula (III) includes a disaccharide unit. In such a disaccharide unit, the monosaccharides may be connected in any suitable way. As the skilled person will appreciate, the nature of the bonding between the two monosaccharide units will determine the nature of the disaccharide.

Preferably the disaccharide is selected from sucrose, lactose, maltose, trehalose, cellobiose, kojibiose, nigerose, isomaltose, sophorose, laminaribiose, gentiobiose, turanose, maltulose, palatinose, gentiobiulose, mannobiose, melibiose, melibiulose, rutinose, rutinulose and xylobiose.

More preferably the disaccharide unit is selected from sucrose, lactose, maltose, trehalose, and cellobiose. An especially preferred disaccharide unit is trehalose.

Preferably each M and M' is independently selected from a mycolic acid residue of formula (IV):

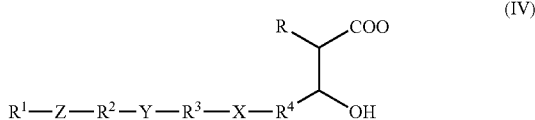

wherein R is an optionally-substituted alkyl, alkenyl, alkynyl, aryl, arylalkyl or alkylaryl moiety having from 1 to 50 carbon atoms; $R^1$ is an optionally-substituted alkyl, alkenyl, alkynyl, aryl, arylalkyl or alkylaryl moiety having from 1 to 40 carbon atoms; each of $R^2$, $R^3$ and $R^4$ is independently selected from an optionally-substituted alkylene, alkenylene, alkynylene, arylene, arylalkylene or alkylarylene moiety having from 1 to 40 carbon atoms; each of X, Y and Z is independently selected from an optionally-substituted alkylene, alkenylene, alkynylene, arylene, alkylarylene, cycloalkylene, alkoxy, ketone, ester, amide, imide, imine, thioether, ether, thioester and thioketone.

Preferably at least one of X, Y and Z includes a moiety selected from cyclopropyl, C=A and C-$AR^5$; wherein A is O, S or $NR^5$, wherein each $R^5$ may be independently H or alkyl.

R is preferably an optionally-substituted alkyl, alkenyl, alkynyl, aryl or alkylaryl moiety having from 4 to 40 carbon atoms, preferably from 6 to 36 carbon atoms, for example from 10 to 32 carbon atoms, preferably from 16 to 30 carbon atoms, for example from 18 to 28 carbon atoms, preferably from 20 to 26 carbon atoms. Most preferably R has from 22 to 24 carbon atoms.

R may be substituted with one or more groups selected from hydroxy, alkoxy (especially methoxy), halo (especially chloro or fluoro), nitro, sulfoxy, alkylsulfoxy, amino, mercapto and trifluoromethyl.

One or more hetero atoms may be incorporated into the chain, for example O, S or N to form an ether, a thioether or an amine. The chain may be alkenyl and thus may include one or more double bonds.

Preferably R is an optionally substituted alkyl or alkenyl group. If R is an alkenyl group, it preferably includes at most one double bond for every six carbon atoms, more preferably at most one double bond for every ten carbon atoms. Any double bonds present may have an E or Z configuration. However in especially preferred embodiments no double bonds are present and R is an alkyl group.

Preferably R is an optionally substituted alkyl or alkenyl moiety which includes no more than one substituent per four carbon atoms, preferably no more than one substituent for every six carbon atoms, preferably no more than one substituent for every ten carbon atoms, and most preferably no more than one substituent for every sixteen carbon atoms in the chain. In some especially preferred embodiments, R is an unsubstituted alkyl chain.

Most preferably R is an optionally-substituted alkyl or alkenyl chain. It may be straight chain or branched. Most preferably it is substantially straight chained and any branching is minimal, for example one or two methyl or ethyl residues may be branched from a long main chain. In especially preferred embodiments R is not branched.

Most preferably R is an unsubstituted alkyl chain having from 16 to 30 carbon atoms. In especially preferred embodiments R is an unsubstituted straight chain alkyl group having from 22 to 24 carbon atoms.

$R^1$ is an optionally-substituted alkyl, alkenyl, alkynyl, aryl or alkylaryl moiety having preferably from 4 to 36 carbon atoms, more preferably from 6 to 32 carbon atoms, for example from 8 to 28 carbon atoms, preferably from 10 to 24 carbon atoms, for example from 12 to 22 carbon atoms. Most preferably $R^1$ has from 16 to 20 carbon atoms.

$R^1$ may be substituted with one or more groups selected from hydroxy, alkoxy (especially methoxy), halo (especially chloro or fluoro), nitro, sulfoxy, alkylsulfoxy, amino, mercapto and trifluoromethyl.

One or more hetero atoms may be incorporated into the chain, for example O, S or N to form an ether, a thioether or an amine. The chain may be alkenyl and thus may include one or more double bonds.

Preferably $R^1$ is an optionally-substituted alkyl or alkenyl group. If $R^1$ is an alkenyl group, it preferably includes at most one double bond for every six carbon atoms, more preferably at most one double bond for every ten carbon atoms. Any double bonds present may have an E or Z configuration. However, in especially preferred embodiments, $R^1$ does not contain any double bonds and is an alkyl chain.

Preferably $R^1$ is a substituted alkyl or alkenyl moiety which includes no more than one substituent per four carbon atoms, preferably no more than one substituent for every six carbon atoms, preferably no more than one substituent for every ten carbon atoms, and most preferably no more than one substituent for every twelve carbon atoms in the chain. In especially preferred embodiments $R^1$ is an unsubstituted alkyl chain.

Most preferably $R^1$ is an optionally-substituted alkyl or alkenyl chain. It may be straight chain or branched. Most preferably it is substantially straight chained and any branching is minimal, for example one or two methyl or ethyl residues may be branched from a long main chain. In especially preferred embodiments $R^1$ is not branched.

Most preferably $R^1$ is an unsubstituted alkyl chain having from 12 to 24 carbon atoms. In especially preferred embodiments R is an unsubstituted straight chain alkyl group having from 16 to 20 carbon atoms.

$R^4$ is preferably an alkylene or alkenylene moiety having from 2 to 36 carbon atoms, preferably from 4 to 30 carbon atoms, for example from 8 to 26 carbon atoms, more preferably from 10 to 20 carbon atoms and most preferably from 12 to 18 carbon atoms.

$R^4$ may be straight chained or may include branching and may optionally include substituents. $R^4$ may be substituted with one or more groups selected from hydroxy, alkoxy (especially methoxy), halo (especially chloro or fluoro), nitro, sulfoxy, alkylsulfoxy, amino, mercapto and trifluoromethyl.

One or more hetero atoms may be incorporated into the chain, for example O, S or N to form an ether, a thioether or an amine. The chain may be alkenyl and thus may include one or more double bonds.

Preferably $R^4$ is an optionally-substituted alkylene or alkenylene group. If $R^4$ is an alkenylene group, it preferably includes at most one double bond for every six carbon atoms, more preferably at most one double bond for every ten carbon atoms. Any double bonds present may have an E or Z configuration. In especially preferred embodiments $R^4$ does not include any double bonds and is an alkylene chain.

Preferably $R^4$ is a substituted alkylene or alkenylene moiety which includes no more than one substituent per four carbon atoms, preferably no more than one substituent for every six carbon atoms, preferably no more than one substituent for every ten carbon atoms, and most preferably no more than one substituent for each sixteen carbon atoms in the chain. In especially preferred embodiments $R^4$ is an unsubstituted alkylene moiety.

$R^4$ may be straight chained or may include some branching. In preferred embodiments, however, $R^4$ is a straight chain alkylene residue having 12 to 18 carbon atoms.

Each of $R^2$ and $R^3$ may be independently selected from an alkylene, alkenylene, alkynylene, arylene, arylalkylene and alkylarylene moiety having from 1 to 30 carbon atoms, preferably 4 to 20, more preferably from 6 to 15 carbon atoms.

Each of $R^2$ and $R^3$ may be straight chained or may include branching and may optionally include substituents. Each may be independently substituted with one or more groups selected from hydroxyl, alkoxy (especially methoxy), halo (especially chloro or fluoro), nitro, sulfoxy, alkylsulfoxy, amino, mercapto and trifluoromethyl.

One or more hetero atoms may be incorporated into either or each chain, for example O, S or N to form an ether, a thioether or an amine. Either or each chain may be alkenylene and thus may include one or more double bonds.

Preferably each of $R^2$ and $R^3$ is an optionally-substituted alkylene or alkenylene group. If either or each is an alkenylene group, it preferably includes at most one double bond for every six carbon atoms, more preferably at most one double bond for every ten carbon atoms. Any double bonds present may have an E or Z configuration. Preferably $R^2$ does not include any double bonds. Preferably $R^3$ does not include any double bonds.

Preferably each of $R^2$ and $R^3$ is an optionally substituted alkylene or alkenylene moiety which includes no more than one substituent per four carbon atoms, preferably no more than one substituent for every six carbon atoms, preferably no more than one substituent for every ten carbon atoms in the chain. Preferably $R^2$ is an unsubstituted alkylene moiety. Preferably $R^3$ is an unsubstituted alkylene moiety.

Most preferably each of $R^2$ and $R^3$ is an alkylene residue which is unsubstituted and straight chained.

Preferably $R^2$ and $R^3$ have a combined total of from 4 to 30, preferably from 10 to 20 carbon atoms.

Each of X, Y and Z may be independently selected from an alkylene group, a cycloalkylene group, a moiety including a ketone, a thioketone or an imine, a moiety including a hydroxyl, thiol or amine moiety, a moiety including an alkoxy residue, a moiety including an epoxide or a moiety including an alkene.

Suitably each of X, Y and Z contributes a two or three carbon fragment. Such a 2 or 3 carbon fragment may suitably include a methyl substituent.

Preferably each of X, Y and Z is independently selected from one or more of the units shown in Figure V:

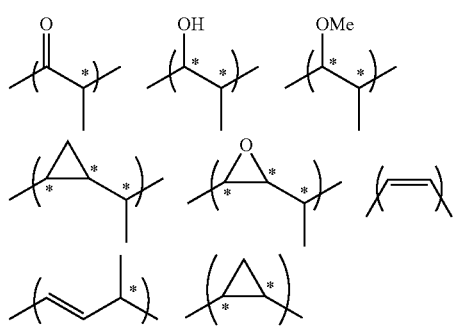

FIG. V

The substituents may be included in either orientation with respect to the mycolic acid motif; hence either regioisomer may be present. Further the unit may include any of the possible stereoisomers resulting from the different chiral centres indicated (*) in Figure III.

In preferred embodiments Y is $CH_2$ and thus the unit "$R^2$—Y—$R^3$" may be regarded in preferred embodiments as an alkylene chain of formula $(CH_2)_n$. n is preferably from 1 to 40, more preferably from 5 to 30, preferably from 10 to 25, for example from 16 to 22.

In preferred embodiments X includes a cyclopropyl moiety. This group may have a cis or a trans configuration. In some preferred embodiments it has trans configuration.

In some preferred embodiments X includes a methyl substituent. The carbon carrying the methyl substituent may have an (R) or (S) configuration.

In some embodiments X may include a unit including a cyclopropyl moiety which contributes two carbon atoms to the main chain or a unit including a cyclopropyl moiety and on an adjacent carbon a methyl substituent, which contributes three carbon atoms to the main chain. In such embodiments the methyl substituent may be between the cyclopropyl unit and the mycolic acid motif, that is proximal to the mycolic acid motif, or it may be distal from the mycolic acid motif. Preferably it is distal from the mycolic acid motif. Any relative stereochemistry between the cyclopropane moiety and methyl group may be present. Suitably the α-methyl cyclopropyl unit has (R), (S), (R), or (S), (R), (S) stereochemistry.

In some embodiments X includes an alkene. This may be a cis or trans alkene. It may be di- or trisubstituted. Preferably it is disubstituted. X may include a methyl substituent at a position α to the alkene moiety. Such an α-methyl substituent may be proximal or distal relative to the mycolic acid functionality.

In preferred embodiments group Z includes a cyclopropyl group or the moiety C=A or C-$AR^5$ wherein A is O, S or $NR^5$. The or each $R^5$ may independently be hydrogen or an alkyl group. When the or each $R^5$ is an alkyl group, it is preferably an alkyl group having 1 to 10 carbon atoms, more preferably from 1 to 4 carbon atoms, for example methyl or ethyl.

In some preferred embodiments group Z includes a moiety having an alkoxy substituent $R^5O$. $R^5$ is $C_1$ to $C_4$ alkyl and thus may be methyl, ethyl, propyl (including isopropyl and n-propyl) or butyl (including n-butyl, tert-butyl, isobutyl and sec-butyl). Preferred are methyl and ethyl. Most preferably $R^5$ is methyl i.e. Z carries a methoxy substituent. The alkoxy group is suitably appended directly to a carbon atom that lies in the main long chain of the molecule.

Preferably Z is a two-carbon fragment which includes an alkoxy (especially methoxy) substituent and a to this group a methyl substituent.

The methyl substituent may have any relative stereochemistry compared with the alkoxy group and each of the carbon atoms bearing the methyl group and the methoxy group may be (R) or (S) independently.

In some preferred embodiments Z includes an α-methyl β-alkoxy moiety, for example an α-methyl β-methoxy moiety.

The methyl group may be distal from the mycolic acid motif relative to the alkoxy functionality or it may be proximal. Preferably the methyl is distal from the mycolic acid motif.

In some preferred embodiments Z includes a cyclopropyl unit. In such embodiments two carbons of the cyclopropyl group lie within the long carbon chain. The cyclopropyl group may have a cis or a trans configuration.

Z may include a unit including a cyclopropyl moiety which contributes two carbon atoms to the main chain or a unit including a cyclopropyl moiety and on an adjacent carbon a methyl substituent, which contributes three carbon atoms to the main chain. In such embodiments the methyl substituent may be between the cyclopropyl unit and the mycolic acid motif, that is proximal to the mycolic acid motif, or it may be distal from the mycolic acid motif. Preferably it is distal from the mycolic acid motif. Any relative stereochemistry between the cyclopropane moiety and methyl group may be present. Suitably the α-methyl cyclopropyl unit has (R), (S), (R), or (S), (R), (S) stereochemistry.

In some preferred embodiments, Z includes the group C=A or C-AH. The carbon atom of the group C=A or C-AH suitably lies in the main long chain of the molecule.

Preferably A is O and the group Z includes a carbonyl or alcohol functionality. The preferred carbonyl group is a ketone.

Preferably Z is a two-carbon fragment which includes ketone or an alcohol and a to this group a methyl substituent.

When Z includes an alcohol, the methyl substituent may have any relative stereochemistry compared with the hydroxyl group and each of the methyl group and hydroxyl group may (R) or an (S) independently have an configuration. When Z includes an α methyl ketone, the methyl group may have either stererochemistry. However this is a readily epimerisable centre and thus a mixture of epimers at this position is sometimes obtained.

Thus in preferred embodiments Z includes an α-methyl ketone or an α-methyl hydroxy moiety. An α-methyl ketone is especially preferred.

The methyl group may be distal to the mycolic acid motif relative to the ketone/alcohol functionality or it may be proximal. Preferably the methyl is distal from the mycolic acid motif.

In especially preferred embodiments, each M or M' is independently selected from the moieties shown in figures VI(a), VI(b), VI(c) and VI(d).

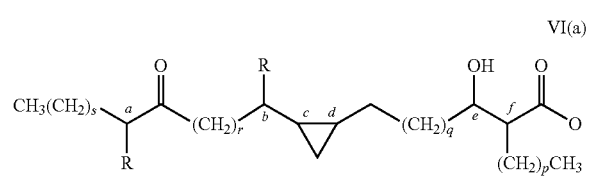

VI(a)

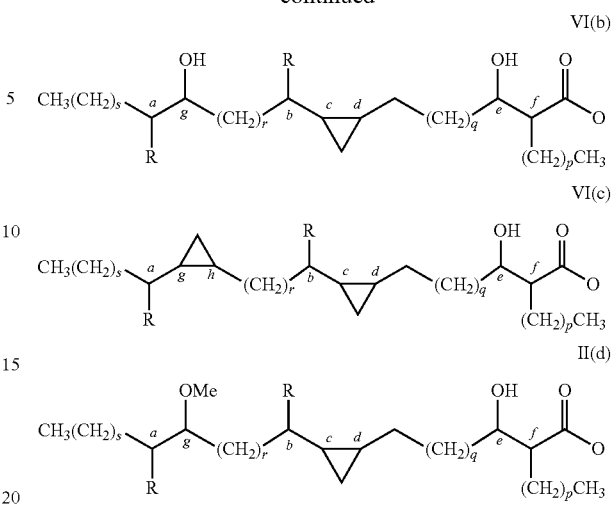

In each of the structures VI(a), VI(b), VI(c) and VI(d) R may be methyl or hydrogen.

In each of the structures VI(a), VI(b), VI(c) and VI(d), is preferably from 4 to 40, preferably from 8 to 36, more preferably from 12 to 32, for example from 16 to 30, more preferably from 20 to 28, for example from 22 to 26.

In the structures VI(a), VI(b), VI(c) and VI(d), q is preferably from 2 to 40, more preferably from 4 to 36, for example from 6 to 30, preferably from 8 to 24, for example from 10 to 20 and preferably from 12 to 18.

In the structures VI(a), VI(b), VI(c) and VI(d), r is preferably from 2 to 40, for example from 6 to 36, preferably from 10 to 32, for example from 12 to 28, and preferably from 14 to 24.

In the structures VI(a), VI(b), VI(c) and VI(d), s is preferably from 2 to 40, for example from 6 to 36, preferably from 10 to 32, for example from 12 to 28, and preferably from 14 to 24.

In the structures VI(a), VI(b), VI(c) and VI(d), each of the chiral centres indicated at a, b, c, d, e, f, g and h may independently have either an (R) or an (S) configuration. The cyclopropyl rings may be selected to have a trans or a cis configuration.

Any or all of the stereocentres indicated by a, b, c, d, e, f, g or h in structures VI(a), VI(b), VI(c) and VI(d), may independently have either an (R) or an (S) configuration. Each cyclopropyl group may have either absolute stereochemistry and have a trans or a cis configuration.

Any of the stereocentres indicated by a, b, c, d, e, f, g or h may be a mixture of epimers. In the case of structure VI(a) it is possible that the stereocentre designated a will be a mixture of epimers as this is a readily epimerisable position.

The stereocentre indicated at position a may have an (R) or an (S) configuration.

The stereocentre at b may have an (R) or an (S) configuration.

The stereocentre at c may have an (R) or an (S) configuration.

The stereocentre at d may have an (R) or an (S) configuration.

The stereocentre at e may have an (R) or an (S) configuration.
The stereocentre at f may have an (R) or an (S) configuration.
The stereocentre at g may have an (R) or an (S) configuration.
The stereocentre at h may have an (R) or an (S) configuration.

In some preferred embodiments, the sterocentres indicated by a, b, c, d, e, f, g and h match those that are found in natural products.

Especially preferred compounds of the present invention include the trehalose monomycolate compounds shown in figure VIIa; the symmetrical trehalose dimycolate compounds shown in figure VIIb; asymmetrical trehalose dimycolate compounds shown in figure VIIc:

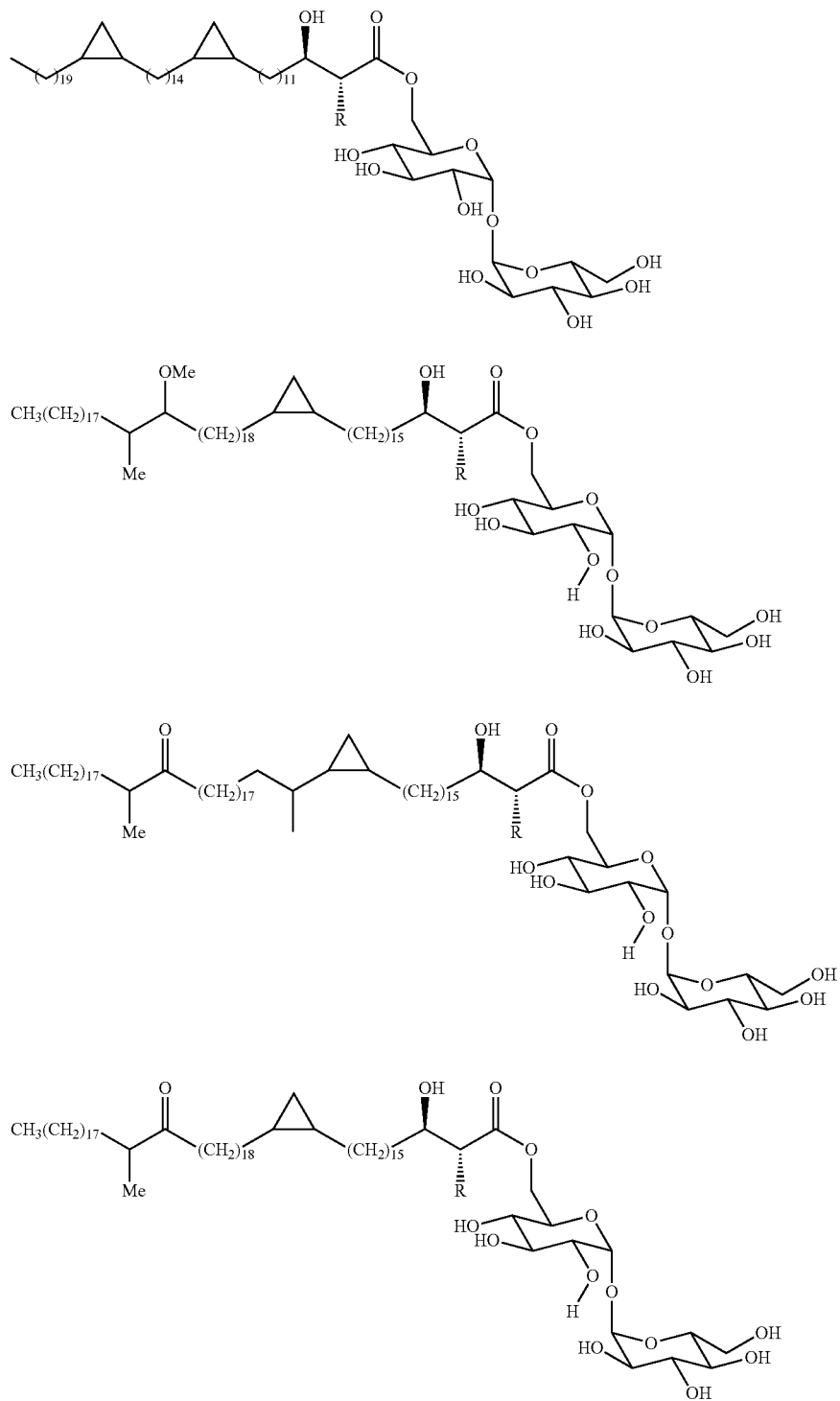

FIG. VIIa

-continued
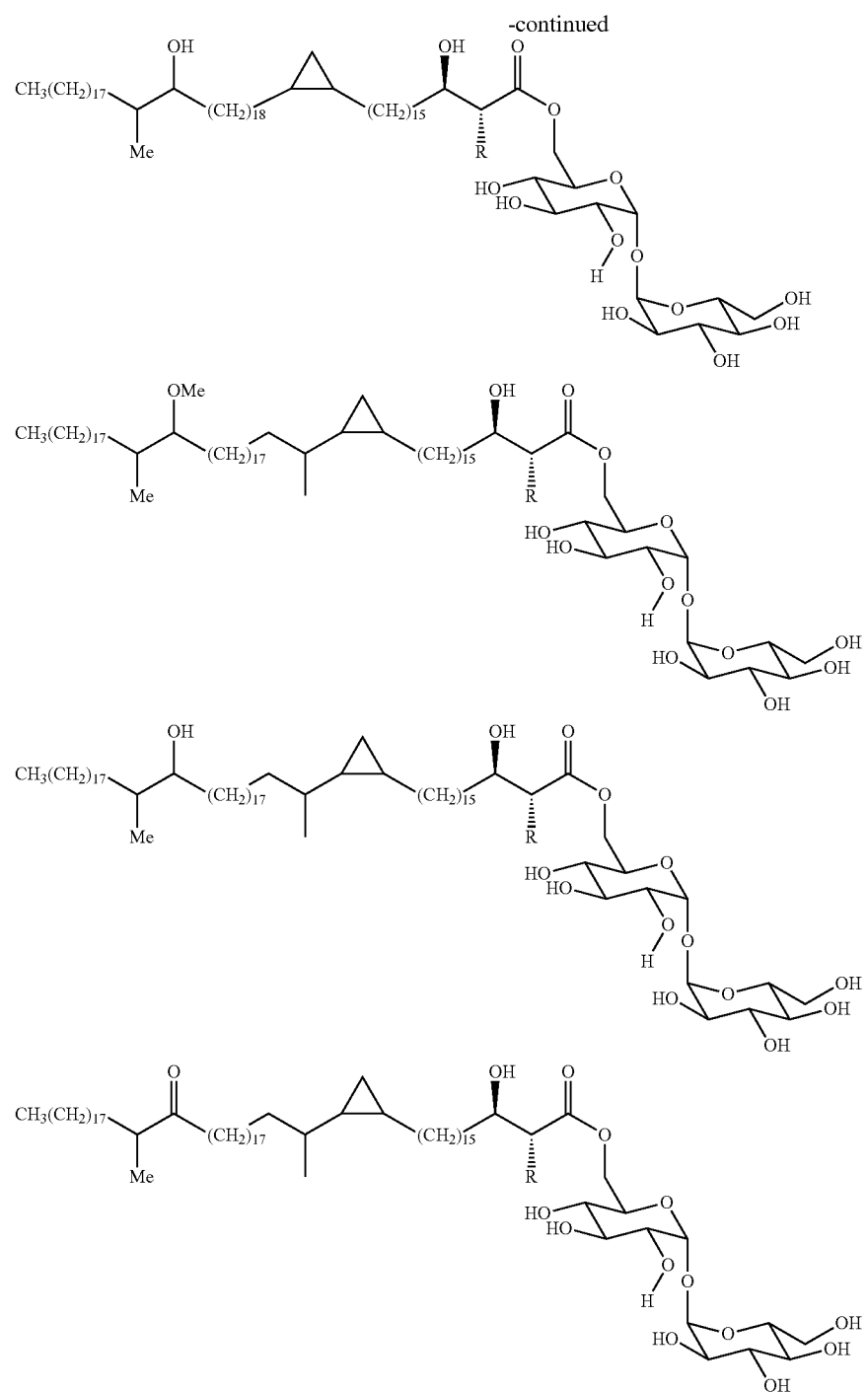
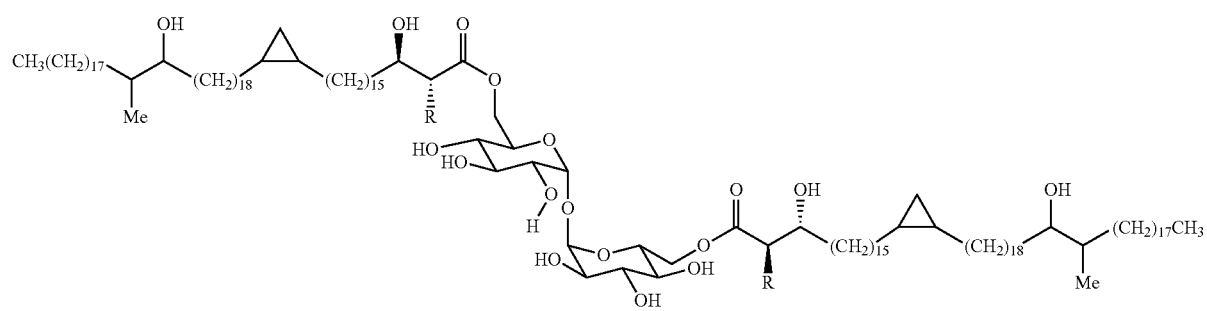
FIG. VIIb

-continued
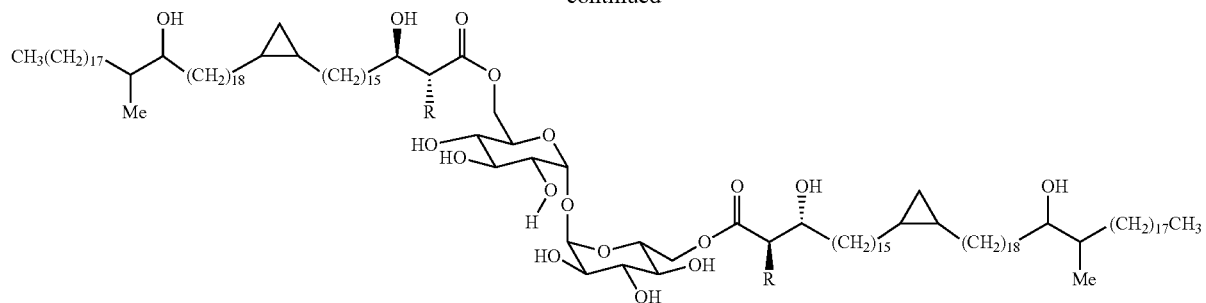
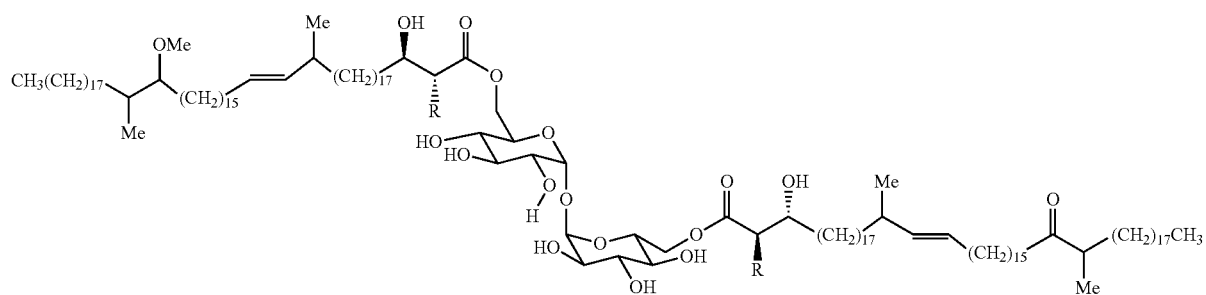
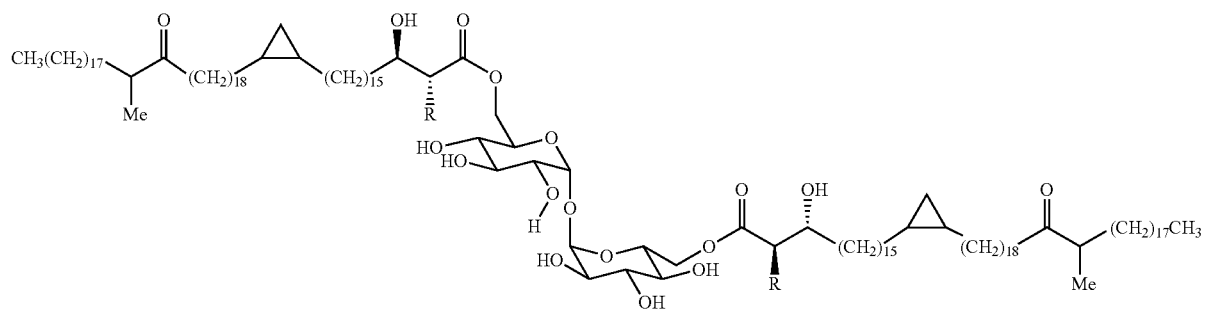
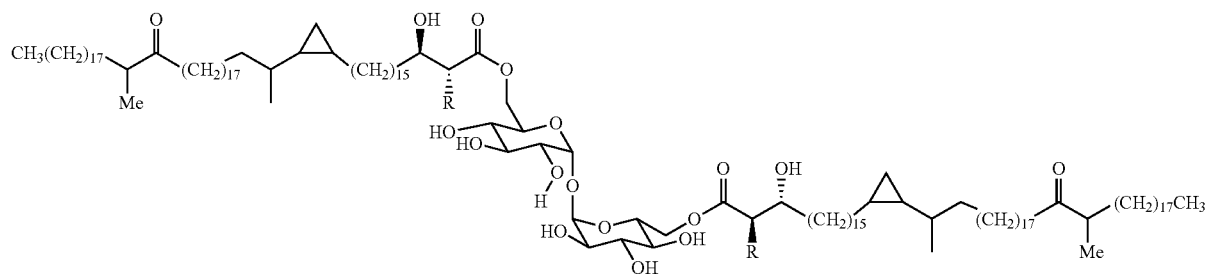
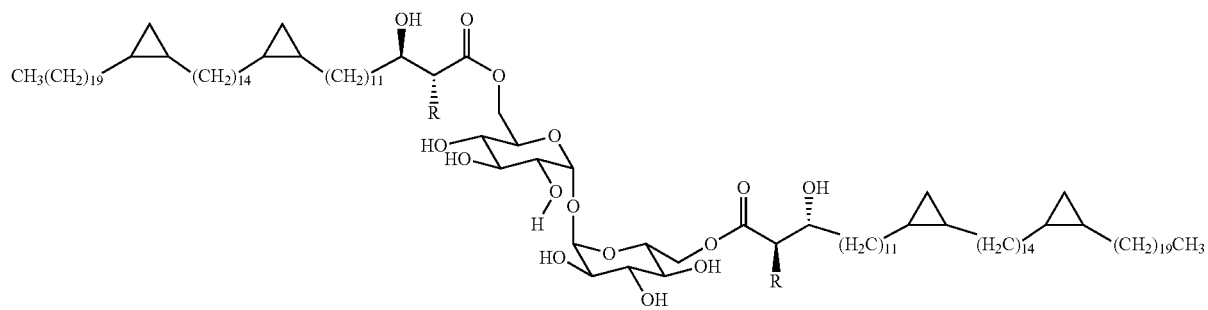

-continued
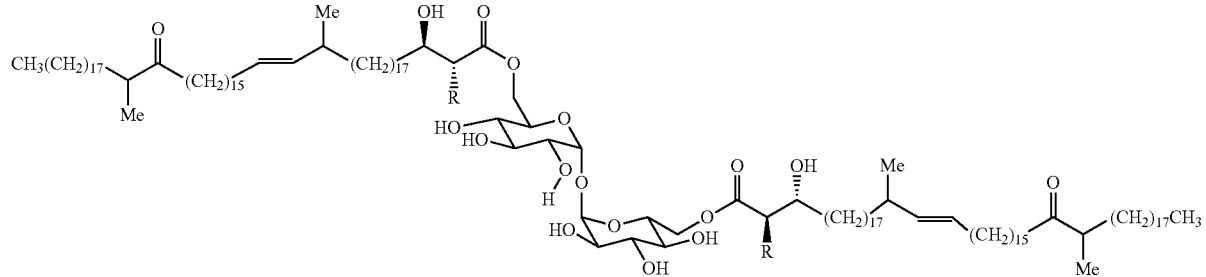
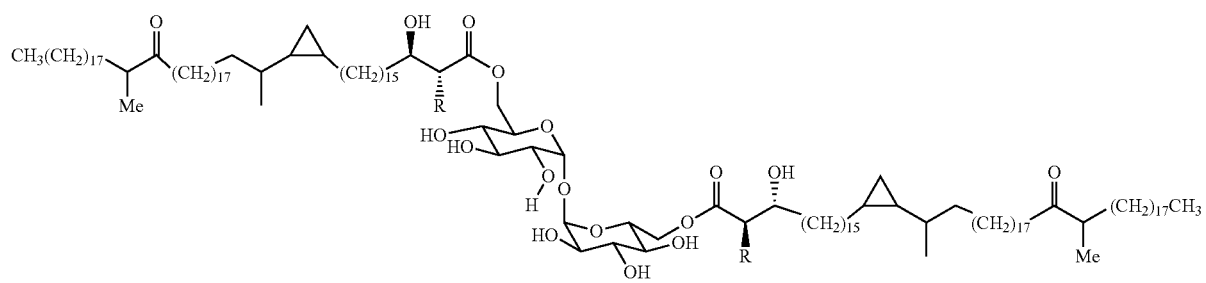
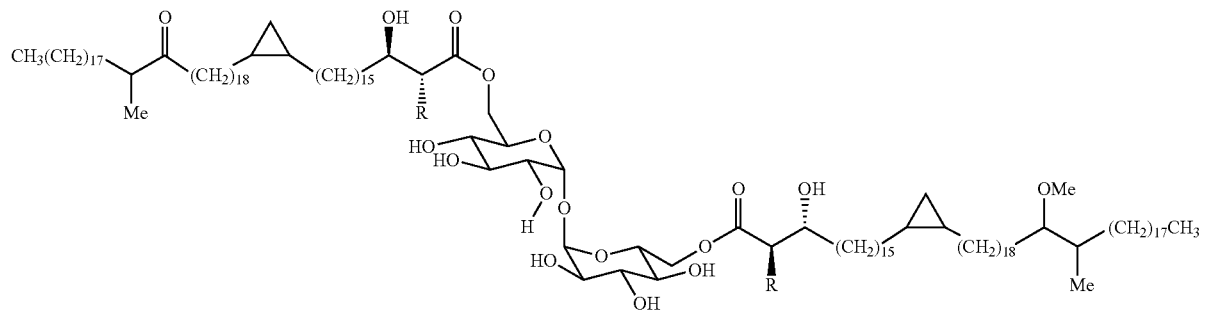
FIG. VIIc
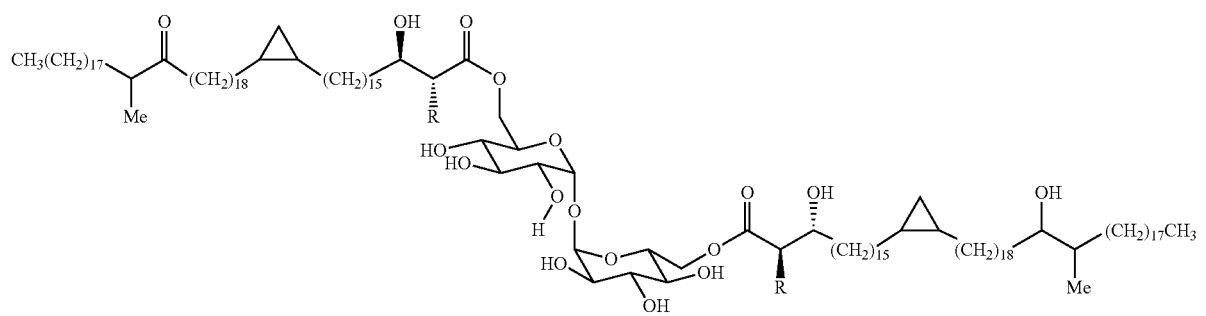
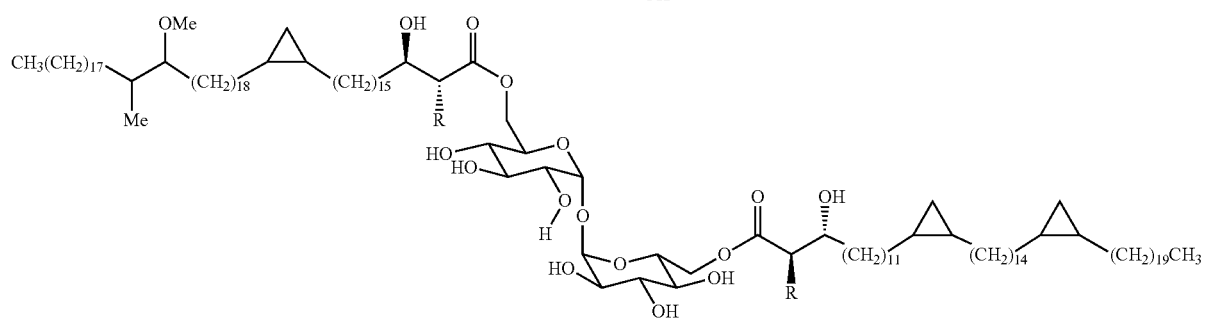

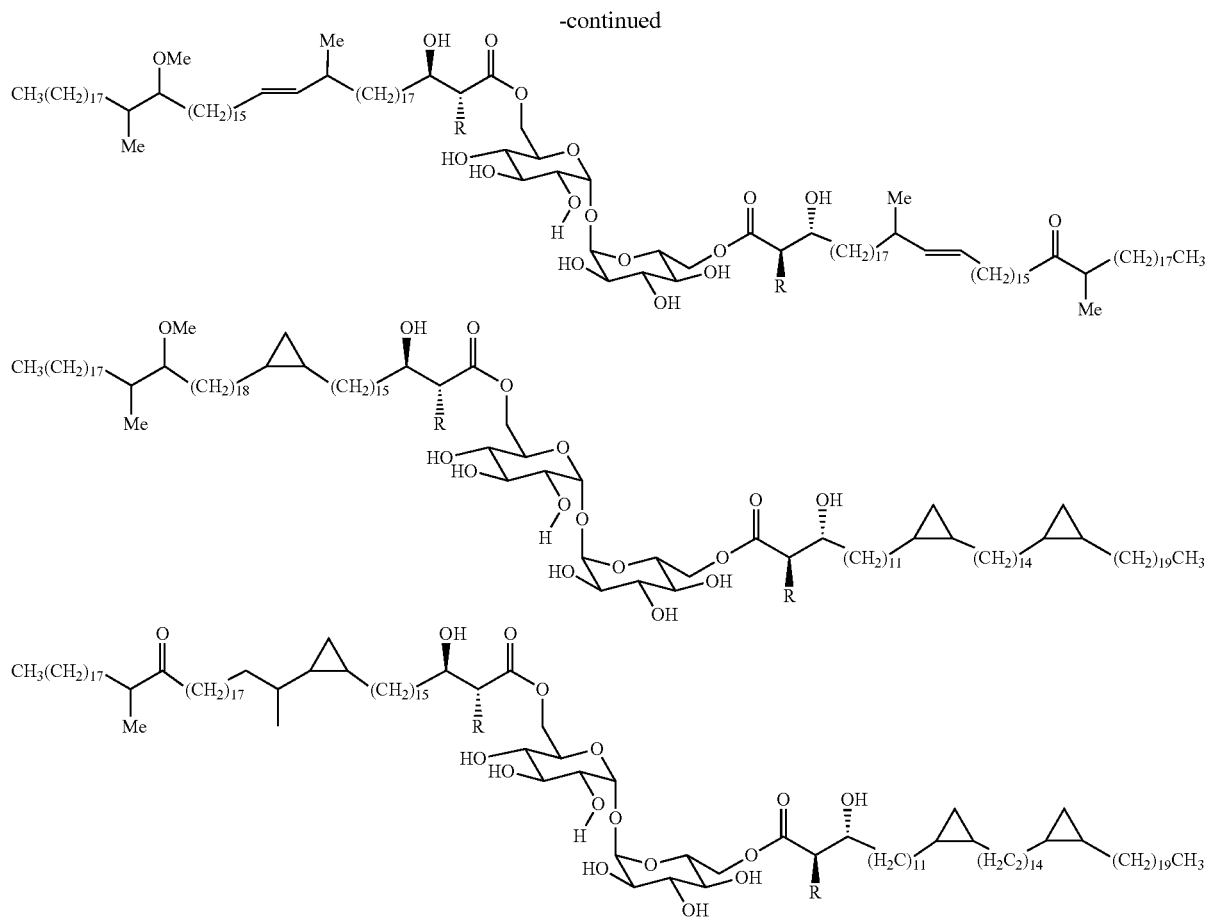

-continued

In each of the compound of figures VIIa, VIIb and VIIc, R is group having the formula $(CH_2)_{21}CH_3$ or $(CH_2)_{23}CH_3$. Preferred compounds of figures VIIa, VIIb and VIIc may have any stereochemical configuration. Especially preferred are compounds having stereogenic centres which match those found in nature.

According to a fourth aspect of the present invention there is provided a composition comprising a mixture of two or more compounds of formula (III).

Such mixtures may include, in addition to quite structurally different compounds derived from different classes of mycolic acids and/or different saccharides, mixtures of different stereo and regioisomers, as well as different homologues. However these mixtures are suitably controlled mixtures deliberately prepared rather than the complex mixtures obtained by extraction from natural sources.

According to a fifth aspect of the present invention there is provided a composition comprising a compound of formula (III) and a pharmaceutically-acceptable carrier.

Preferred features of fourth and fifth aspects are suitably as defined in relation to the first, second and third aspects.

In some embodiments the composition of the fifth aspect may include more than one compound of formula (III).

Any suitable pharmaceutically-acceptable carrier may be used and is suitably selected from those known to the person skilled in the art.

The pharmaceutically-acceptable carrier may be a solid, for example polymer dust or a sugar; a micelle, for example a liposome; a liquid, for example a water-in-oil emulsion, or a solution, typically a saline solution or phosphate buffered saline; a gas; or a transdermal delivery system. When the carrier is a liquid, the composition may be in the form of a suspension or a vaporised liquid, typically a nebulisable physiological saline solution. In some embodiments the composition may be in a "semi-solid" or gel form. It may be in the form of a paste, cream or lotion. It may comprise a film-forming material.

In some embodiments, the composition may include a mixture of different classes of mycolic acid moiety and/or different saccharides and/or different homologues and/or different stereoisomers and/or different regioisomers. However it is preferred that the composition comprises a single compound of formula (III) consisting essentially of a single isomer. In embodiments in which mixtures are present these suitably contain controlled mixtures where the structures of the individual components and the relative amounts thereof are known.

The composition of the fifth aspect may further comprise one or more optional excipients, for example colourants, flavourings, fillers, antioxidants, stabilisers and taste-masking agents.

The form of the composition of the fifth aspect of the present invention will depend on the method by which it is intended to be administered. The composition of the fifth aspect may be formulated to enable it to be administered in any suitable form.

The composition may be provided in solid ingestible form, for example as a pill or capsule. One such possible formulation is a polymeric capsule the surface or lumen of which carries compound(s) of formula (III). It may be provided in a liquid ingestible form, for example as a syrup or elixir.

In some embodiments there may be provided a kit comprising a composition comprising a compound of formula (III) and a composition comprising a carrier. These two compositions may suitably be combined prior to use. This may be useful if, for example, the dosage form is not stable to long periods of storage.

In some embodiments the composition may be provided as a liquid which can be delivered nasally or as a dry powder, suspension or solution which can be inhaled.

Preferably, compositions for inhalation are presented for administration to the respiratory tract as a snuff or an aerosol or solution for a nebulizer, or as a microfine powder for insufflation, alone or in combination with an inert carrier, for example lactose. In such a case the particles of active compound suitably have diameters of less than 50 microns, preferably less than 10 microns, for example between 1 and 5 microns, such as between 2 and 5 microns.

In some preferred embodiments the composition is provided in a form suitable for topical administration. It may be in any form suitable for application to body surfaces of a human or an animal, for example the skin, eyes, mouth, nose, throat, ears, vagina and anus. Preferably the composition is provided in a form suitable for application to the skin. It may be in the form of a paste, gel, cream, lotion, ointment or unguent.

In some especially preferred embodiments the composition is a skin soothing or skin healing composition. In such embodiments it may further comprise other components which sooth the skin or promote healing. Such components are well known to those skilled in the art. Examples include panthenol and panthenol derivatives, aloe vera, pantothenic acid, pantothenic acid derivatives, allantoin, bisabolol, and dipotassium glycyrrhizinate, and vitamins and derivatives thereof.

Skin healing or skin soothing compositions suitably comprise from 0.0001 to 20 wt % of one or more compounds of formula (III), preferably from 0.0005 to 10 wt %, more preferably from 0.001 to 7.5 wt %, for example from 0.01 to 5 wt %.

According to a sixth aspect of the present invention there is provided a compound of formula (III) for use in therapy.

Preferred features of the sixth aspect are as defined in relation to the first, second, third, fourth and fifth aspects.

In some preferred embodiments the sixth aspect of the present invention provides a compound of formula (III) for use in the treatment of diseases of the immune system, in particular the immune system of mammals and especially humans.

Suitably the disease treated is a disease involving an out of control or pathology causing immune response, for example an allergic immune disease or an autoimmune disease.

Preferably the compounds of the present invention are useful in the treatment of a disease in which Th2-lymphocyte activity contributes to the immune disease.

Examples of diseases which may be treated according to the present invention include asthma, rhinitis, hayfever, eczema and other allergic diseases; and autoimmune diseases, for example, systemic lupus erythematosus, Goodpasture's syndrome, Grave's disease, Myasthenia Gravis, type I diabetes and multiple sclerosis.

In some preferred embodiments, the present invention is useful in the treatment of asthma and other allergic diseases. Allergic diseases are known to the person skilled in the art and include, but are not limited to, allergic asthma, allergic rhinitis, allergic conjunctivitis, eczema, airway hyperactivity and eosinophilic airway inflammation.

Although the present invention relates primarily to the treatment of diseases of the immune system of humans, it may also be used to treat diseases of the immune system of other mammals, for example, allergic diseases such as skin diseases.

Sugar esters of mycolic acids are known to interact with cytokines which play an important role in the immune system. Mixtures of cord factors which are found in nature have been shown to affect many different cytokines. Because the present invention allows sugar esters of mycolic acids (including cord factors) to be prepared as single compounds, the effect of the individual compounds on individual cytokines can be examined and exploited.

In some preferred embodiments the present invention provides compounds of formula (III) for use in the treatment of a skin disease.

The compounds may be used in the treatment of a skin disease of a human or other animal, for example livestock.

The compounds may be used in treating skin diseases for example eczema or psoriasis.

The present invention further provides compounds of formula (III) for use in promoting skin healing. Thus they may help to repair damage to the skin or heal lesions. They may be used to promote skin healing in humans or animals, especially livestock.

According to a seventh aspect of the present invention there is provided a method of treating a mammal having a disease of the immune system by administering to said mammal a compound of formula (III).

Preferred features of the seventh aspect are as defined in relation to the first, second, third, fourth, fifth and sixth aspects.

In the method of the seventh aspect, the compound of formula (III) may be administered by any suitable means. It is suitably administered in the form of a composition of the fifth aspect. The compounds of the present invention may be administered via inhalation, intravenously, orally, subcutaneously, by intramuscular injection, by suppository or enema form, intranasally, by topical application, buccally, sublingually or transdermally.

Preferably the compounds are administered in a non-invasive manner, most preferably by inhalation.

The method of treatment of the present invention may be curative or it may be prophylactic. For example in the treatment of asthma, dosing of the compounds of the present invention in advance may prevent a user from suffering an allergic asthmatic reaction upon subsequent exposure to an allergen.

In some embodiments it may be preferable to administer compounds of formula (III) in combination with a known antigen. Such antigens are suitably those known to be involved in an allergic disease or autoimmune disease.

In some embodiments, a subject is first treated with a compound of formula (III) and after a suitable period is exposed to an antigen. Exposure to an antigen may occur naturally from the environment, from within the body itself or there may be controlled exposure to an antigen.

Preferably the compound of formula (III) is administered in the form of a unit-dose composition, such as a unit dose nasal or inhaled composition.

Dependent on the form of the unit-dose composition, devices suited for delivery typically are pressurized aerosols, nebulisers and dry powder inhalers designed for efficient and reproducible delivery, flexible dosing and allowing for patient control on intake of the composition.

According to a eighth aspect of the present invention there is provided a compound of formula (III) for use as an adjuvant in vaccination.

Preferably the compounds are used as an adjuvant for vaccines aimed at raising cellular immune responses where the level of immune protection raised will benefit from a cellular immune defence component.

Non-limiting examples of diseases in which raising of the cellular immune defence is desired include tuberculosis and other diseases caused by mycobacteria, pneumonitis induced by respiratory syncytial virus, cancer, malaria, and other diseases caused by bacterial, viral, fungal and parasitic infectious agents.

The compounds of formula (III) may be used as an adjuvant in a vaccine for human use or in a vaccine for use on other mammals.

The present invention may provide an adjuvant useful for the vaccination of livestock against diseases against which a cellular immune defence is required. Examples include bovine tuberculosis, avian flu and blue tongue.

The present invention may be also useful in providing an adjuvant for use in the vaccination of domestic or wild animals.

The present invention further provides a vaccine composition comprising a compound formula (III) and an antigen.

Any antigen may be used. The antigen may be provided in any suitable form, such as will be well understood by the person skilled in the art. For example it may be the pathogen inactivated by heat or fixated with formaldehyde, or a protein thereof or a peptide part of the protein combined or not with a hapten carrier, or a fusion protein of an antigenic protein or peptide and a carrier protein, or non-protein antigenic structures.

Preferably the vaccine composition further comprises a carrier. Any pharmaceutically acceptable carrier may be used and those suitable include those described in relation to the fourth aspect.

Preferred carriers for the vaccine composition are liposomes. Liposomes are phospholipid bilayers and are commonly used to deliver drugs to a target.

Methods of formulating vaccine compositions using liposomes are well-known to those skilled in the art.

The present invention further provides a method of vaccinating a mammal against a disease, the method comprising administering to said mammal a compound of formula (III) and an antigen.

According to a ninth aspect of the present invention there is provided the use of a compound of formula (III) in a method of detecting a pathogen.

The pathogen is suitably one or more bacteria, in particular one or more mycobacteria. Preferably the pathogen is one which causes an infectious disease. Thus the present invention may provide compounds of formula (III) for use in the diagnosis of an infectious disease, the method comprising detecting a pathogen which causes the disease.

Infectious diseases caused by bacteria include tuberculosis and leprosy. The bacteria may include one or more *mycobacterium bovis, mycobacterium avium, mycobacterium marinum, mycobacterium ulcerans, mycobacterium kansasi* and *mycobacterium tuberculosis*. Most preferably the eighth aspect of the present invention involves detecting *mycobacterium tuberculosis*, that is the bacteria which causes tuberculosis in humans; or *mycobacterium bovis*, that is the bacteria which causes bovine tuberculosis.

Suitably compounds of formula (III) are able to be recognised by characteristic components of or present in the immune cells of humans or animals infected with a pathogen. Preferably compounds of formula (III) of the present invention are able to be recognised by antibodies produced by the body in response to the presence of a pathogen, especially the pathogen *mycobacterium tuberculosis*.

Suitably the method of the ninth aspect of the present invention is an in vitro detection method. The method preferably involves contacting a composition comprising a compound of formula (III) with an antibody containing sample. The antibody suitably binds to the compound of the first aspect. The bound antibody can then be detected. Means for detecting the antibody are known to those skilled in the art. One suitable method involves binding a secondary antibody to the first wherein the secondary antibody includes an enzymatic or other marker. Observation of the marker thus indicates the presence of the primary antibody. In this way it is possible to detect the presence of a pathogen, for example *mycobacterium tuberculosis* in the sample and thus diagnose infection with a disease, for example tuberculosis.

Preferably the sample containing characteristic components of or present in the immune cells comprises body fluid, for example the body fluid of a person or animal suspected of having an infectious disease, for example tuberculosis. The sample may comprise blood, serum, plasma, pleural effusion, ascites fluid or urine of a person infected with tuberculosis.

The presence of the antibody in the sample may be detected due to the interaction of the antibody with the compound of the first aspect. This interaction is observed using a suitable assay. Suitable assays are known to those skilled in the art and include for example the ELISA assay, the RAE assay, immunofluorimetry and plasmon surface resonance.

In a further aspect the present provides a method of treating a mammal having a skin complaint by administering to said mammal a compound of formula (III). The skin complaint may be a skin infection, sore or irritated skin or a skin wound or lesion. Suitably said method comprises applying to the affected area of skin a composition of the fifth aspect.

Where appropriate, any feature of any aspect of the present invention may be combined with any feature of any other aspect.

The present invention will now be further described with reference to the following non-limiting examples.

EXAMPLE 1

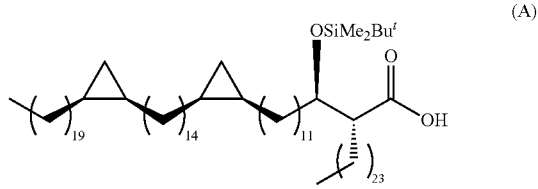

(A)

The compound having the structure shown in figure A above was prepared according to the following method:

Imidazole (0.117 g, 1.72 mmol) was added to a stirred solution of (R)-2-((R)-1-Hydroxy-12-{(1R,2S)-2-[14-((1R, 2S)-2-icosyl-cyclopropyl)-tetradecyl]-cyclopropyl}-dodecyl)-hexacosanoic acid (0.39 g, 0.34 mmol) in anhydrous DMF (3 ml) and dry toluene (4 ml) at room temperature followed by the addition of tert-butyldimethylsilylchloride (0.517 g, 3.4 mmol) and 4-dimethyl amino pyridine (0.042 g, 0.34 mmol). The reaction mixture was stirred at 70° C. for 24 hrs and at room temperature for 18 hrs. When TLC showed that no starting material left, the solvent was removed under high vacuum and the residue was diluted with petroleum ether/ethyl acetate (10:2) (50 ml) and water (20 ml). The organic layer was separated and the aqueous layer was re-extracted with petroleum ether/ethyl acetate (2×30 ml). The combined organic layers were washed with water, dried and evaporated to give a colourless oil residue. The residue was dissolved in THF (11 ml), water (1.4 ml), and methanol (1.4 ml), to this was added potassium carbonate (0.20 g). The reaction mixture was stirred at 45° C. for 18 hrs, and then TLC showed no starting material left. The sample was evaporated to ¼$^{th}$ of the volume and diluted with (5:1) petroleum ether/diethyl ether (30 ml) then acidified with potassium hydrogen sulfate to pH 2. The organic layer was separated and the aqueous layer was re-extracted with petrol/ethyl acetate (2×20 ml). The combined organic layers were washed with water, dried and evaporated to give a residue, which was purified by column chromatography on silica eluting with petroleum ether/ethyl acetate (10:1) to provide the compound shown in figure A (0.28 g, 68%). [α]$^{30}_D$=+4.012 (c=1.13 g, CHCl$_3$) which showed δ$_H$: 3.85-3.88 (1H, br, q, J 5.35 Hz), 2.53 (1H, br, pent, J 4.7 Hz), 1.75-1.10 (134H, m), 0.91 (9H, s), 0.89 (6H, t, J 7 Hz), 0.66-0.64 (4H, m), 0.57 (2H, dt, J 4.1, 8.15 Hz), 0.12 (3H, s), 0.10 (3H, s), −0.32 (2H, br, q, J 5.35 Hz); δ$_C$: 177.32, 73.57, 50.65, 35.08, 31.94, 30.24, 29.71, 29.58, 29.52, 29.49, 29.43, 29.11, 28.74, 27.53, 25.74, 24.65, 22.69, 17.95, 15.78, 14.11, 10.91, −4.29, −4.93; u$_{max}$: 3500-2500 (very broad, OH for the carboxylic group), 2919, 2850, 1707, 1466, 1361, 1254, 1215, 1075, 939, 836, 761, 669, 420 cm$^{-1}$.

EXAMPLE 2

(B1)

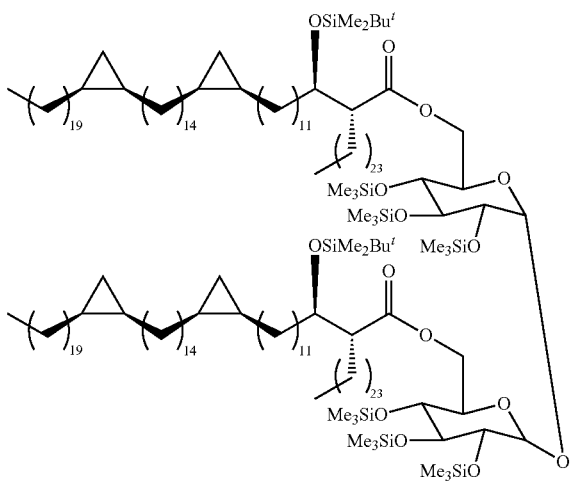

(B2)

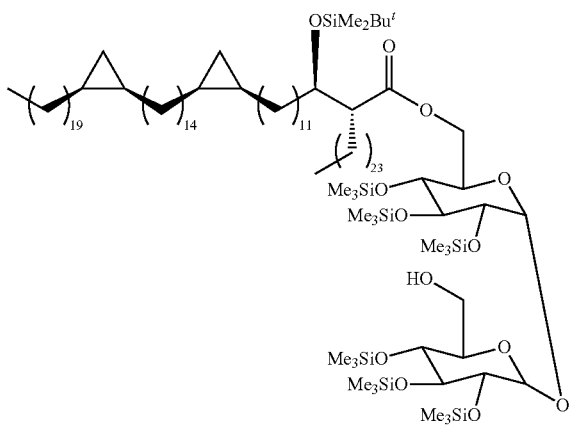

1-(3-Dimethylaminopropyl)-3-ethylcarbodimidehydrochloride (EDCl) (125 mg, 0.65 mmol) and 4-dimethylaminopyridine (70 mg, 0.57 mmol) were added to a stirred solution of the compound prepared in example 1 (figure A), (256 mg, 0.204 mmol), 2,3,4,2',3',4'-hexakis-O-(trimethylsilyl)-α,α'-trehalose (63 mg, 0.082 mmol) and powdered 4 A° molecular seives in dry dichloromethane (3 ml) at room temperature under nitrogen atmosphere. The reaction mixture was stirred for 6 days at r.t then TLC showed no starting material was left. The reaction mixture was diluted with dichloromethane and filtered. The filtrate was evaporated under reduced pressure to give a residue, which was purified by column chromatography on silica eluting with petroleum ether/ethyl acetate (20:1) to give a first fraction comprising (R)-2-((R)-1-(tert-Butyl-dimethyl-silanyloxy)-12-{(1R,2S)-2-[14-((1R,2S)-2-icosyl-cyclopropyl)-tetradecyl]-cyclopropyl}-dodecyl)-hexacosanoic anhydride, 0.148 g), a second fraction comprising the compound shown in figure B1 (40.2 mg, 15%) as a colourless thick oil; and a third fraction comprising the compound shown in figure B2 (0.1142 g, 70%);

The anhydride (0.148 g) was collected, dried and evaporated. The same procedure as described above was followed to give a first fraction (anhydride, 0.0045 g), a second fraction comprising the compound shown in figure B1 (0.11 g, 57%) and a third fraction comprising the compound shown in figure B2 (25.4 mg, 21%).

The compound of figure B1 (0.15 g, 33%), a colourless thick oil showed [α]$^{28}_D$=+23.08 (c=1.32 g, CHCl$_3$), {Found [M+Na]$^+$: 3266.79 (one peak of isotope pattern); C$_{198}$H$_{398}$O$_{15}$Si$_8$Na requires: 3266.9497}; which showed δ$_H$ (500 MHz, CDCl$_3$): 4.86 (2H, d, J 2.8 Hz), 4.37 (2H, br, d, J 10.4 Hz), 4.04-3.99 (4H, m), 3.94 (2H, br, q, J 5.35 Hz), 3.9 (2H, t, J 9.1 Hz), 3.53 (2H, t, J 8.9 Hz), 3.38 (2H, dd, J 2.8, 9.1 Hz), 2.56 (2H, ddd, J 3.5, 4.75, 10.1 Hz), 1.55-1.05 (268H, m), 0.89 (12H, t, J 7 Hz), 0.88 (18H, s), 0.65 (8H, br, m), 0.57 (4H, dt, J 4.1, 8.2 Hz), 0.166 (18H, s), 0.15 (18H, s), 0.14 (18H, s), 0.067 (12H, s), −0.32 (4H, br, q, J 5.35 Hz); δ$_C$:

173.82, 130.47, 94.85, 73.56, 73.43, 72.84, 71.83, 70.75, 62.39, 51.86, 33.47, 31.94, 30.24, 30.04, 29.82, 29.67, 29.52, 29.5, 29.46, 29.38, 28.74, 28.14, 26.25, 25.99, 25.93, 25.89, 25.19, 22.70, 18.03, 15.79, 14.12, 10.92, 1.10, 0.95, 0.17, −4.51, −4.64; $u_{max}$: 2922, 2852, 1743, 1466.7, 1252, 1077, 838 cm$^{-1}$;

The compound of figure B2 (0.139 g, 49%) showed; $\{[\alpha]^{28}_D=+33.54$ (c=0.96 g, CHCl$_3$)$\}$, {Found [M+Na]$^+$: 2032.6900; C$_{114}$H$_{234}$O$_{13}$Si$_7$Na requires: 2032.6614}; which showed $\delta_F$, (500 MHz, CDCl$_3$): 4.91 (1H, d, J 2.85 Hz), 4.84 (1H, d, J 3.15 Hz), 4.35 (1H, dd, J 2.2, 11.65 Hz), 4.08 (1H, dd, J 4.1, 12 Hz), 3.99 (1H, br, dq, J 2.5, 9.5 Hz), 3.95 (1H, m), 3.91 (2H, dt, J 6.65, 9.15 Hz) 3.85 (1H, td, J 3.45, 9.45 Hz), 3.74-3.66 (2H, m), 3.48 (2H, dt, J 6, 9.15 Hz), 3.43 (1H, dd, J 3.15, 9.15 Hz), 3.39 (1H, dd, J 3.15, 9.15 Hz), 2.55 (1H, ddd, J 3.5, 5.4, 9.15 Hz), 1.72 (1H, dd, J 5.1, 7.6 Hz), 1.64-1.60 (2H, m), 1.44-1.08 (132H, m), 0.89 (6H, t, J 7 Hz), 0.88 (9H, s), 0.67-0.64 (4H, m), 0.57 (2H, dt, J 4.1, 8.2 Hz), 0.174 (9H, s), 0.164 (9H, s), 0.159 (9H, s), 0.155 (9H, s), 0.153 (9H, s), 0.127 (9H, s), 0.065 (3H, s), 0.061 (3H, s), −0.32 (2H, q, J 5 Hz); $\delta_C$: 174.07, 94.52, 94.40, 73.44, 73.38, 73.37, 72.89, 72.84, 72.78, 72.01, 71.44, 70.75, 62.46, 61.67, 51.84, 41.36, 33.44, 31.94, 30.24, 29.79, 29.71, 29.67, 29.38, 28.74, 28.11, 26.41, 25.93, 25.83, 24.87, 22.70, 19.44, 18.44, 18.02, 15.78, 14.11, 10.92, 1.06, 1.01, 0.93, 0.85, 0.18, 0.04, −4.48, −4.68; $u_{max}$; 2924, 2853, 1742, 1465, 1251, 1165, 1110, 1076, 1006, 898, 873, 842, 748 cm$^1$.

material was left. The reaction was cooled to 5° C. and quenched with saturated solution of sodium bicarbonate (3 ml) then diluted with cold CHCl$_3$ (50 ml). The organic layer was separated and the aqueous layer was re-extracted with CHCl$_3$ (2×50 ml). The combined organic layer were washed with brine solution (50 ml), dried and evaporated to give a residue, which was purified by column chromatography on silica eluting with CHCl$_3$/MeOH (0.85:0.15) to give the compound shown in figure C (0.051 g, 53%) as a colourless thick oil. $[\alpha]^{26}_D=+15.02$ (c=3.2 g, CHCl$_3$), {Found [M+Na]$^+$: 2833.9 (one peak of isotope pattern); 0; C$_{180}$H$_{350}$O$_{15}$Si$_2$Na requires: 2833.8628}; which showed $\delta_H$ (500 MHz, CDCl$_3$+ few drops of CD$_3$OD): 5.05 (2H, d, J 3.15 Hz), 4.29 (2H, br, dd, J 4.4, 12.3 Hz), 4.2 (2H, br, d, J 10.75 Hz), 3.91 (2H, br, d, J 9.2 Hz), 3.87 (2H, br, q, J 5.4 Hz), 3.80 (2H, br, t, J 9.45 Hz), 3.45 (2H, dd, J 3.5, 9.8 Hz), 2.93 (2H, br, dt, J 4.31 Hz), 2.52 (2H, ddd, J 3.8, 6.35, 10.4 Hz), 1.6-1.01 (300H, m), 0.83 (12H, t, J 7.25 Hz), 0.82 (18H, s), 0.63-0.56 (4H, m), 0.52 (2H, dt, J 4.1, 8.2 Hz), 0.0002 (6H, s), −0.02 (6H, s), −0.38 (2H, br, q, J 5.35 Hz); $\delta_C$: 175.15, 93.43, 85.44, 73.27, 72.79, 71.76, 70.37, 70.27, 62.85, 57.7, 51.51, 35.24, 33.75, 32.38, 31.94, 30.5, 30.4, 30.26, 30.24, 30.1, 29.98, 29.94, 29.83, 29.74, 29.7, 29.58, 29.54, 29.5, 29.44, 29.36, 29.28, 28.73, 27.79, 27.58, 27.1, 26.17, 25.93, 25.82, 24.3, 22.7, 17.98, 15.76, 14.88, 14.11, 10.93, −4.4, −4.75; $u_{max}$: 3384, 2920, 2851, 2360, 1739, 1469, 1253, 1077, 837, 775, 721 cm$^{-1}$.

EXAMPLE 3

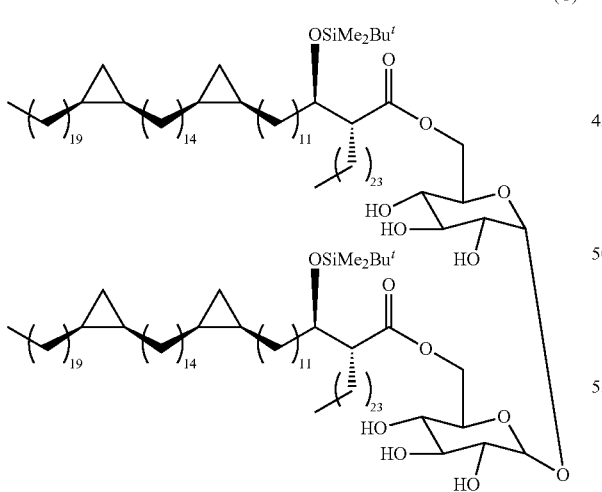

(C)

Tetrabutylammonium fluoride (0.27 ml, 0.27 mmol, 1M) was added to a stirred solution of the compound prepared in example 2 having the structure shown in figure B1 (0.11 g, 0.035 mmol) in dry THF (7 ml) at 5° C. under nitrogen atmosphere. The reaction mixture was allowed to reach room temperature and stirred for 1 hr then TLC showed no starting

EXAMPLE 4

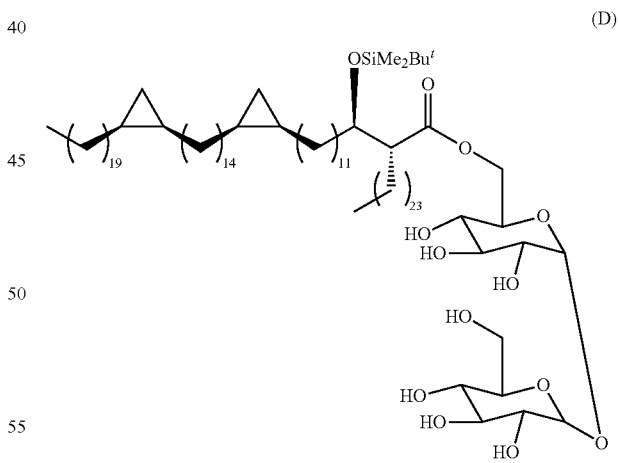

(D)

Tetrabutylammonium fluoride (0.538 ml, 0.538 mmol, 1M) was added to a stirred solution of the compound prepared in example 2 having the structure shown in figure B2 (0.139 g, 0.0691 mmol) in dry THF (7 ml) at 5° C. under nitrogen atmosphere. The reaction mixture was allowed to reach room temperature and stirred for 1 hr, until TLC showed no starting material was left. The reaction mixture was worked up as described above and purified by column chromatography on silica eluting with CHCl$_3$/MeOH (8.5:1.5) to give the compound shown in figure (D) (0.098 g, 90%) as a colourless syrup. {[α]$^{26}_D$=+11.94 (c=2.95, CHCl$_3$)}; {[Found M+Na]$^+$: 1599.17 (one peak of isotope pattern); C$_{96}$H$_{186}$O$_{13}$SiNa requires: 1599.6093}; which showed δ$_H$: (500 MHz, CDCl$_3$+ few drops of CD$_3$OD): 5.03 (2H, d, J 2.2 Hz), 4.22 (1H, br, s), 4.00 (1H, br, dt, J 2.85, 9.4 Hz), 3.92 (1H, br, d, J 9.7 Hz), 3.73-3.77 (3H, m), 3.65 (1H, m), 3.41 (4H, m), 2.45 (1H, m), 1.17-1.30 (143H, m), 0.79 (15H, m, including a triplet resonated at δ 0.80, J 7.25 Hz), 0.56 (4H, m), 0.47 (2H, dt, J 4.1, 8.5 Hz), −0.04 (3H, s), −0.06 (3H, s), −0.42 (2H, q, J 5.3 Hz); δ$_C$: 93.43, 73.00, 72.74, 72.57, 72.27, 72.09, 70.13, 62.81, 52.06, 49.20, 49.01, 31.74, 30.03, 29.58, 29.51, 29.47, 29.17, 28.53, 25.66, 25.03, 23.86, 22.50, 19.56, 15.59, 13.92, 13.50, 10.72, −4.69, 4.94, u$_{max}$: 3384.8, 2922.5, 2852.2, 1731.3, 1466.7, 1381.7, 991.9, 482.6 cm$^{-1}$.

EXAMPLE 5

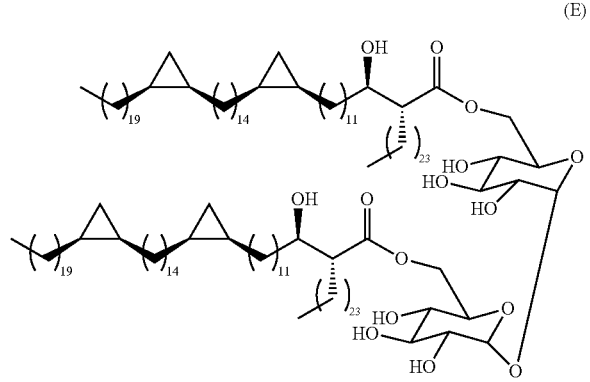

(E)

A dry polyethylene vial equipped with a acid proof rubber septum was charged with the compound shown in figure (C) prepared in example 3 (0.05 g, 0.018 mmol), pyridine (100 μl) in dry THF (4.5 ml) and stirred at room temperature under argon. To it was added hydrogen fluoride-pyridine complex as ~70% hydrogen fluoride (0.253 ml) at 5° C. The mixture was then stirred at 43° C. for 17 h, when TLC showed no starting material was left, then neutralized by pouring slowly into sat. aq. sodium bicarbonate until no more CO$_2$ was liberated. The product was extracted with chloroform (3×50 ml), then the combined organic layers were dried, evaporated to give a residue which was purified by chromatography eluting with CHCl$_3$/MeOH (10:1) to give the compound shown in figure E (0.024 g, 54%) as a syrup. {[α]$^{27}_D$=+27.91, (c=2.2, CHCl$_3$)}; {Found [M+Na]$^+$: 2604.7600 (one peak of isotope pattern); C$_{168}$H$_{322}$O$_{15}$Na requires: 2605.40}; which showed δ$_C$: 175.40, 94.91, 72.52, 72.45, 71.28, 71.19, 69.83, 64.37, 52.20, 34.66, 31.79, 30.12, 30.08, 29.69, 29.58, 29.56, 29.43, 29.33, 29.22, 28.59, 27.18, 25.11, 22.54, 15.65, 13.90, 10.78, 10.75. u$_{max}$: 3391, 2918, 2850, 1730, 1467, 1260, 1020, 800, 464 cm$^{-1}$.

EXAMPLE 6

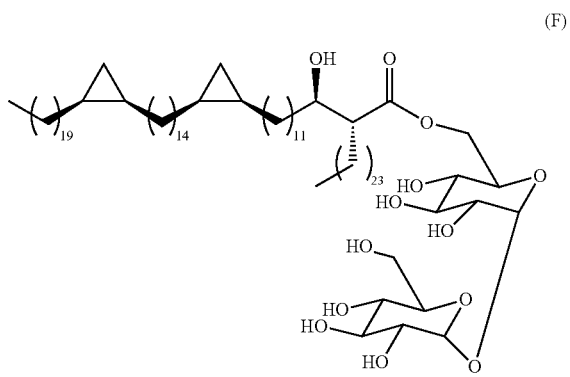

(F)

A dry polyethylene vial equipped with a rubber septum was charged with the compound shown in figure (D) (0.083 g, 0.053 mmol), pyridine (0.1 ml) in dry tetrahydrofuran (5 ml) and stirred at room temperature under nitrogen atmosphere. To it was added hydrogen fluoride-pyridine complex as ~70% hydrogen fluoride (0.75 ml). The mixture was stirred at 43° C. for 17 hrs, when TLC showed no starting material was left, then neutralized by pouring slowly into sat. aq. sodium bicarbonate until no more CO$_2$ was liberated. The product was extracted with chloroform (3×50 ml), then the combined organic layers were dried, evaporated to give a residue which was purified by chromatography eluting with CHCl$_3$/MeOH (10:1) then (1:1) to give the crude product (0.024 g, 32%) as a syrup. The sample was then purified by dissolving it in chloroform to which cold methanol was added, after which a precipitate was formed. It was then centrifuged for 10 minutes at 8000 rev/min and the compound shown in figure F as a white solid (0.017 g, 22%) {[α]$^{26}_D$=+41.53, (c=1.83, CHCl$_3$)}; {Found [M+Na]$^+$: 1485.14 (one peak of isotope pattern); C$_{90}$H$_{172}$O$_{13}$Na requires: 1485.31}; which showed δ$_H$ (500 MHz, CDCl$_3$+few drops of CD$_3$OD): 5.11 (1H, br, s), 5.07 (1H, br, s), 4.62 (1H, br, d, J 8.2 Hz), 4.13 (1H, br, m), 4.06 (1H, br, m), 3.92-3.82 (5H, m), 3.58 (1H, br, d, J 7.5 Hz), 3.53 (1H, br, d, J 8.85 Hz) 3.36 (2H, t, J 6.5), 2.69 (1H, br, s), 2.41-2.39 (1H, br, m), 1.72 (1H, m), 1.61 (3H, m), 1.50-1.11 (143H, m), 0.87-0.84 (6H, t, J 7 Hz), 0.62 (1H, m), 0.56-0.51 (1H, dt, J 4.1, 8.2 Hz), −0.36 (1H, q, J 5.35 Hz); δ$_C$: 175.45, 94.13, 72.63, 72.52, 72.32, 71.42, 70.87, 70.12, 64.1, 62.1, 58.8, 52.10, 31.85, 30.21, 30.18, 30.15, 29.79, 29.63, 29.59, 29.54, 29.42, 29.29, 28.67, 28.64, 23.85, 22.61, 19.61, 15.70, 15.68, 14.01, 13.49, 10.86, 10.83; u$_{max}$: 3356, 2919, 2850, 1728, 1468, 1148, 1106, 992, 721, 427 cm$^{-1}$.

EXAMPLE 7

Compounds having the following structure were prepared using a method analogous to that described in examples 1 to 6:

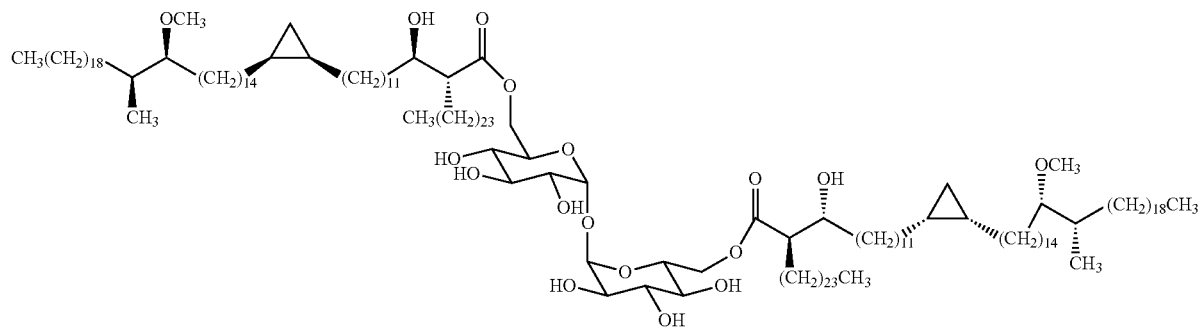

(G)

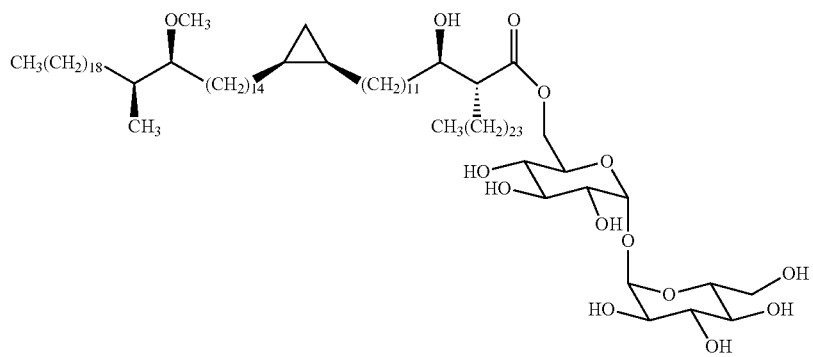

(H)

EXAMPLE 8

Differential Innate Immune Reactivity of Synthetic Trehalose-Mycolates on Human Macrophages Trehalose-mycolates were used to stimulate human RAW 264.7 macrophage cells using literature methods, such as is described in Vivek Rao, Feng Gao, Bing Chen, William R. Jacobs Jr., and Michael S. Glickman. JCI. 116:1660-1667 (2006); Vivek Rao, Nagatoshi Fujiwara, Steven A. Porcelli, and Michael S. Glickman. JEM. 201(4): 535-543 (2005); IKUYO SAKAGUCHI, NORIKAZU IKEDA, MIKI NAKAYAMA, YOSHIKO KATO, IKUYA YANO, AND KENJI KANEDA. INFECTION AND IMMUNITY 68(4): 2043-2052 (2000); and Matsunaga I, Oka S, Inoue T, Yano I. FEMS Microbiol Lett. 55(1-2):49-53 (1990).

Briefly, a sample of each of compounds E, F, G and H was suspended at a concentration of 1 mg/ml in isopropanol, sonicated for 15 minutes in a bath sonicator (Model 1200, Branson Ultrasonic Corporation) at 60° C. The resulting solution was layered onto 24-well tissue culture plates at 10 μg/well and left overnight on the LAF-bench at room temperature to ensure complete evaporation of the solvent. Control wells were layered with solvent without any active compound and a commercial *Mycobacterium tuberculosis* derived trehalose-dimycolate sample obtained from Sigma was used as a reference. To this layer, RAW 264.7 cells were added at $5 \times 10^5$ cells/well in 0.5 ml of DMEM-medium, supplemented with 10% endotoxin-free foetal calf serum, glutamin, sodium-pyruvate, penicillin and streptomycin, and incubated at 37° C. with 5% $CO_2$. Twenty hours after stimulation, supernatants were collected for analysis of inflammatory cytokine production by using a commercial mouse inflammation cytrometric bead array-kit (BD), according to the manufacturer's recommendations, run on a FACSCalibur (Beckton Dickinson) and analysed by FCAP Array v1.0.1 (Soft Flow Inc.).

The results shown in figures 1 and 2 show the differential effectiveness of the compounds at stimulating the induction of the inflammatory cytokine, TNF-alpha, and the monocyte/macrophage and neutrophil attracting chemokine, MCP-1. These results illustrate the potential to fine-tune the immune activities of trehalose-mycolates by altering the chemical fine-structure of the compounds, thus increasing the overall inflammatory immune activity as compared to the natural (Sigma) trehalose-mycolate as in the case of example 5, or to the contrary selectively decreasing inflammatory immune activity as in the case of the TNF-alpha-neutral behaviour of compound (G) of example 7.

The decreased inflammatory immune activity observed for compound (H) of example 7 means that this compound could be useful as an adjuvant for vaccination.

The compound of example 5 shows increased inflammatory immune activity. Because inflammation is followed by tissue repair, this compound may be useful in skin healing applications.

EXAMPLE 9

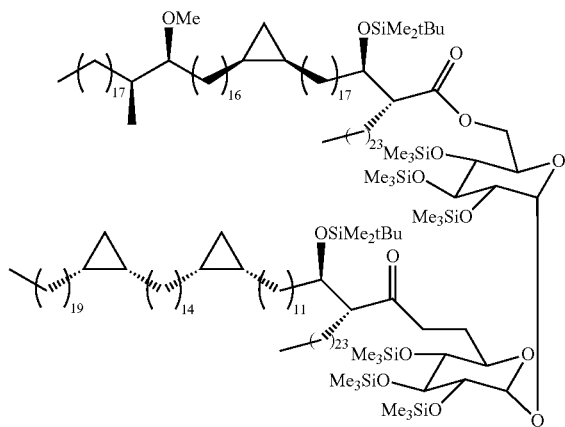

J

A protected trehalose dimycolate compound having the structure shown in figure J above containing two different synthetic mycolic acids was prepared using the following method.

1-(3-Dimethylaminopropyl)-3-ethylcarbodimidehydrochloride (EDCl) (28.8 mg, 0.15 mmol) and 4-dimethylaminopyridine (16 mg, 0.13 mmol) were added to a stirred solution of 6-O—(R)-2-{(R)-1-(tert-butyldimethylsilanyloxy)-18-[(1R,2S)-2-((17S,18S)-17-methoxy-18-methylhexatriacontyl)cyclopropyl]octadecyl}-hexacosanoic-2,3,4,2',3',4'-hexa-kis-O-(trimethylsilyl)-α,α'-trehalose (0.04 g, 0.0188 mmol) and (R)-2-((R)-1-(tert-butyldimethylsilanyloxy)-12-{(1S,2R)-2-[14-((1S,2R)-2-eicosylcyclopropyl)tetradecyl]-cyclopropyl}dodecyl) hexacosanoic acid (35 mg, 0.028 mmol), and powdered 4 A° molecular sieves in dry dichloromethane (0.75 ml) at room temperature under a nitrogen atmosphere. The reaction mixture was stirred for 6 days at room temperature then the reaction mixture was diluted with dichloromethane and filtered. The filtrate was evaporated under reduced pressure to give a residue, which was purified by column chromatography on silica eluting with petrol/ethyl acetate (20:1) to give the compound shown in figure J (10.5 mg, 33.2%) as a colourless thick oil. $[\alpha]^{24}_D$=+17.64 (c=0.85 g, CHCl$_3$), {Found [M+Na]$^+$: 3380.31 (one peak of isotope pattern); C$_{205}$H$_{414}$O$_{16}$Si$_8$Na requires: 3379.96}; which showed $\delta_H$ (500 MHz, CDCl$_3$): 4.85 (2H, d, J 2.85 Hz), 4.37 (2H, br, d, J 9.75 Hz), 4.04-3.98 (4H, m), 3.94 (2H, br, q, J 5.1 Hz), 3.9 (2H, t, J 9.0 Hz), 3.52 (2H, t, J 9.0 Hz), 3.38 (2H, dd, J 2.85, 9.5 Hz), 3.35 (3H, s), 3.96 (1H, br, pent, J 5 Hz), 2.57-2.53 (2H, m), 1.6-0.95 (281H, m), 0.92-0.87 (30H, m, 4×CH$_3$, 2×$^t$Bu), 0.85 (3H, d, J 7 Hz), 0.68-0.63 (6H, m), 0.57 (3H, dt, J 3.8, 8 Hz), 0.16 (18H, s), 0.145 (18H, s), 0.136 (18H, s), 0.078 (3H, s), 0.061 (9H, s), −0.32 (3H, br, q, J 5.05 Hz); $\delta_C$: 173.83, 94.83, 85.44, 73.53, 73.40, 72.80, 71.80, 70.70, 62.37, 57.7, 51.84, 35.31, 33.43, 32.35, 31.90, 30.50, 30.20, 29.97, 29.94, 29.70 (very broad), 29.5, 29.36, 28.70, 28.12, 27.57, 26.16, 25.83, 25.16, 22.69, 18.01, 15.76, 14.87, 14.11, 10.91, 1.09, 0.94, 0.154, −4.52, −4.65; u$_{max}$: 3056, 2921, 2850, 1741, 1461, 1251, 1162, 1099 cm$^{-1}$.

EXAMPLE 10

The MALDI mass spectrum of compound G prepared in example 7 is shown in Figure 3. This clearly shows a single peak (isotope pattern) in the region X to X indicative of the presence of a single compound. The [M+Na]$^+$ starts at m/z 2836 and the small peak isotope pattern at 2852 is [M+K]$^+$.

The invention claimed is:

1. A method of detecting a pathogen, the method comprising:
contacting a body fluid of a person or animal suspected of having an infectious disease with a composition comprising a compound which is at least 90% pure of formula (III):

wherein x is from 1 to 6, y is from 1 to 12, z is from 0 to 10, each M and each M' is independently a mycolic acid residue including a β-hydroxy acid moiety and each S is a monosaccharide unit;
wherein each M and M' is independently selected from a mycolic acid residue of formula (IV):

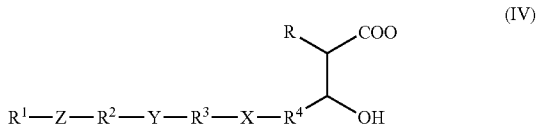

wherein R is an unsubstituted alkyl chain having 16 to 30 carbon atoms; R$^1$ is an alkyl chain having from 12 to 24 carbon atoms; R$^4$ is an alkylene moiety having from 6 to 20 carbon atoms; each of R$^2$ and R$^3$ is an alkylene moiety having from 6 to 20 carbon atoms and R$^2$ and R$^3$ have a combined total of 10 to 20 carbon atoms; Y is CH$_2$; X includes a cyclopropyl unit; and Z includes a cyclopropyl group or the moiety C=A or C-AR$^5$, wherein A is O, S, or NR$^5$; and the each R$^5$ may independently be hydrogen or an alkyl group; and
determining whether an antibody in the body fluid has bound to the compound of formula III.

2. A method according to claim 1, wherein x is 1, y is 2 and z is 0 or 1.

3. A method according to claim 2, wherein the compound of formula III comprises a trehalose unit.

4. The method of claim 1, wherein the composition further comprises:
a pharmaceutically acceptable carrier.

5. The method of claim 1, wherein determining whether the antibody in the body fluid has bound to the compound of formula III includes detecting a second, marked antibody bound to the antibody in the body fluid.

6. The method of claim 1, wherein the body fluid is selected from a group consisting of: blood, serum, plasma, pleural effusion, ascites fluid, and urine.

7. The method of claim 1, wherein the pathogen is *Mycobacterium tuberculosis*.

8. A method of treating a disease of the immune system in a mammal, the method comprising:
administering to the mammal an effective amount of a composition comprising a compound which is at least 90% pure of formula (III):

   (III)

wherein x is from 1 to 6, y is from 1 to 12, z is from 0 to 10, each M and each M' is independently a mycolic acid residue including a β-hydroxy acid moiety and each S is a monosaccharide unit;
wherein each M and M' is independently selected from a mycolic acid residue of formula (IV):

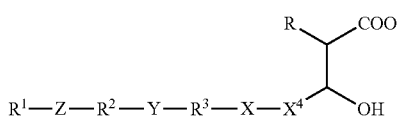   (IV)

wherein R is an unsubstituted alkyl chain having 16 to 30 carbon atoms; $R^1$ is an alkyl chain having from 12 to 24 carbon atoms; $R^4$ is an alkylene moiety having from 6 to 20 carbon atoms; each of $R^2$ and $R^3$ is an alkylene moiety having from 6 to 20 carbon atoms and $R^2$ and $R^3$ have a combined total of 10 to 20 carbon atoms; Y is $CH_2$; X includes a cyclopropyl unit; and Z includes a cyclopropyl group or the moiety C=A or C-$AR^5$, wherein A is O, S, or $NR^5$; and the each $R^5$ may independently be hydrogen or an alkyl group.

9. A method of vaccination of a mammal, the method comprising administering to the mammal a vaccine composition comprising an antigen and a compound which is at least 90% pure of formula (III):

   (III)

wherein x is from 1 to 6, y is from 1 to 12, z is from 0 to 10, each M and each M' is independently a mycolic acid residue including a β-hydroxy acid moiety and each S is a monosaccharide unit;
wherein each M and M' is independently selected from a mycolic acid residue of formula (IV):

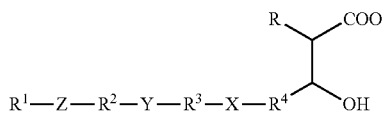   (IV)

wherein R is an unsubstituted alkyl chain having 16 to 30 carbon atoms; $R^1$ is an alkyl chain having from 12 to 24 carbon atoms; $R^4$ is an alkylene moiety having from 6 to 20 carbon atoms; each of $R^2$ and $R^3$ is an alkylene moiety having from 6 to 20 carbon atoms and $R^2$ and $R^3$ have a combined total of 10 to 20 carbon atoms; Y is $CH_2$; X includes a cyclopropyl unit; and Z includes a cyclopropyl group or the moiety C=A or C-$AR^5$, wherein A is O, S, or $NR^5$; and the each $R^5$ may independently be hydrogen or an alkyl group.

\* \* \* \* \*